United States Patent
Almon et al.

(10) Patent No.: US 12,194,079 B2
(45) Date of Patent: Jan. 14, 2025

(54) THERAPEUTIC REGIMEN FOR THE TREATMENT OF FABRY USING STABILIZED ALPHA-GALACTOSIDASE

(71) Applicant: Protalix Ltd., Carmiel (IL)

(72) Inventors: Einat Almon, Timrat (IL); Raul Chertkoff, Adi (IL); Sari Alon, Kibbutz Moran (IL); Yoseph Shaaltiel, Timrat (IL)

(73) Assignee: Protalix Ltd., Carmiel (IL)

( * ) Notice: Subject to any disclaimer, the term of this patent is extended or adjusted under 35 U.S.C. 154(b) by 59 days.

(21) Appl. No.: 16/476,084

(22) PCT Filed: Jan. 5, 2018

(86) PCT No.: PCT/IL2018/050018
§ 371 (c)(1),
(2) Date: Jul. 4, 2019

(87) PCT Pub. No.: WO2018/127920
PCT Pub. Date: Jul. 12, 2018

(65) Prior Publication Data
US 2020/0155654 A1  May 21, 2020

Related U.S. Application Data

(60) Provisional application No. 62/442,537, filed on Jan. 5, 2017.

(51) Int. Cl.
*A61K 38/47* (2006.01)
*C12N 15/85* (2006.01)

(52) U.S. Cl.
CPC .............. *A61K 38/47* (2013.01); *C12N 15/85* (2013.01); *C12Y 302/01022* (2013.01)

(58) Field of Classification Search
None
See application file for complete search history.

(56) References Cited

U.S. PATENT DOCUMENTS

| | | | |
|---|---|---|---|
| 5,256,804 | A | 10/1993 | Ampleman |
| 5,766,897 | A | 6/1998 | Braxton |
| 2013/0295065 | A1 | 11/2013 | Shulman et al. |
| 2015/0320844 | A1 | 11/2015 | Stefano et al. |
| 2016/0053247 | A1 | 2/2016 | Shulman et al. |
| 2016/0184409 | A1 | 6/2016 | Treco et al. |
| 2016/0324839 | A1 | 11/2016 | Castelli et al. |

FOREIGN PATENT DOCUMENTS

| WO | WO 2009/024977 | 2/2009 |
|---|---|---|
| WO | WO 2011/061736 | 5/2011 |
| WO | WO 2011/107990 | 9/2011 |
| WO | WO 2012/098537 | 7/2012 |
| WO | WO 2014/120900 | 8/2014 |

OTHER PUBLICATIONS

Sarkissian, C.N., et al. 2005 Molecular Genetics and Metabolism 86: S22-S26. (Year: 2005).*
International Preliminary Report on Patentability Dated Jul. 18, 2019 From the International Bureau of WIPO Re. Application No. PCT/IL2018/050018. (13 Pages).
International Search Report and the Written Opinion Dated May 4, 2018 From the International Searching Authority Re. Application No. PCT/IL2018/050018. (19 Pages).
Eng et al. "A Phase 1/2 Clinical Trial of Enzyme Replacement in Fabry Disease: Pharmacokinetic, Substrate Clearance, and Safety Studies", American Journal of Human Genetics, 68(3): 711-722, Published Online Feb. 1, 2001.
Supplementary European Search Report and the European Search Opinion Dated Nov. 4, 2020 From the European Patent Office Re. Application No. 18736643.0. (8 Pages).
Schiffmann et al. "Novel Treatment for Fabry Disease—IV Administration of Plant Derived Alpha-Gal-A Enzyme Safety and Efficacy, 1 Year Experience", Journal of Inherited Metabolic Disease, XP036042342, 39(1): 35-284, # O-053, Aug. 12, 2016.
Expert's and Search Report Dated Aug. 13, 2020 From the Ministerio de Economia, Fomento y Turismo, Instituto Nacional de Propiedad Industrial, INAPI, Gobierno de Chile Re. Application No. 2019-001857 and Its Translation Into English. (34 Pages).
Request for Examination and Search Report Dated Sep. 14, 2021 From the Federal Government Institution, Federal Institute of Industrial Property of the Federal Service of Intellectual Property, Patents and Trademarks of the Russian Federation, FIPS Re. Application No. 2019123280 and Its Translation of Office Action Into English. (14 Pages).
Request for Examination Dated Apr. 15, 2021 From the (ROSPATENT), Federal Government Institution of Industrial Property of the Federal Service of Intellectual Property, Patents and Trademark of the Russian Federation Re. Application No. 2011103072 and Its Translation Into English. (15 Pages).
Technical Response and Search Report Dated Apr. 9, 2021 From the Ministerio de Economia, Fomento y Turismo, Instituto Nacional de Propiedad Industrial, INAPI, Gobierno de Chile Re. Application No. 201901867 and its English Translation. (39 Pages).
Protalix Pegunigalsidase Alfa (PRX-102) In Development for The Treatment Of Fabry Deseases, Protalix Biotherapeutics: 13 P., Downloaded From Internet, 2021.
Request for Examination Dated Feb. 14, 2022 From the (ROSPATENT), Federal Government Institution of Industrial Property of the Federal Service of Intellectual Property, Patents and Trademark of the Russian Federation Re. Application No. 2019124280 and Its Translation Into English. (8 Pages).

(Continued)

Primary Examiner — Marsha Tsay

(57) ABSTRACT

Methods of treating Fabry disease via administration of stabilized plant recombinant human alpha galactosidase protein comprising at least two alpha-galactosidase monomers being covalently linked to one another via a linking moiety, and unit dosages of protein are disclosed herein. The disclosed protocols are safe, have greater than 2 week intervals between administrations and exhibit important improvement in patient's disease parameters, in terms of reduced Gb3 accumulation, pain and GI parameters, kidney and cardiac stabilization in the clinical setting.

6 Claims, 7 Drawing Sheets

Specification includes a Sequence Listing.

(56) References Cited

OTHER PUBLICATIONS

Examination Report Dated Apr. 4, 2022 From the Instituto Mexicano de la Propiedad Industrial, Direccion Divisional de Patentes Re. Application No. MX/a/2019/008076 and Its Summary in English. (7 Pages).
Notice of Reason(s) for Rejection Dated Dec. 21, 2021 From the Japan Patent Office Re. Application No. 2014-513308 and Its Translation Into English. (7 Pages).
Clinical Trials History of Changes for Study: NCT02795676; Study of the Safety and Efficacy of PRX-102 Compared to Agalsidase Beta on Renal Function (BALANCE), U.S. National Library of Medicine, Clinical Trials.Gov, Archive, 7.P., First Published Jun. 10, 2019.
Hughes et al. "Novel Treatment for Fabry disease: IV Administration of Plant Derived Alpha-Gal-A Enzyme Safety and Efficacy Interirn Reoprt", Molecular Genetics and Metabolism, 117(2):S59, Feb. 2016.
Examination Report Dated Sep. 28, 2021 From the Instituto Mexicano de la Propiedad Industrial, Direccion Divisional de Patentes Re. Application No. MX/a/2019/008076 together with an English Summary. (9 Pages).
Examination Report Dated Nov. 29, 2022 From the Instituto Mexicano de la Propiedad Industrial, Secretaria de Economia, Direccion Divisional de Patentes Re. Application No. MX/a/2019/008076 and Its Translation Into English. (12 Pages).
Notification of Office Action and Search Report Dated Nov. 22, 2022 From the State Intellectual Property Office of the People's Republic of China Re. Application No. 201880016068.5. (6 Pages).
Translation Dated Dec. 12, 2022 of Notification of Office Action Dated Nov. 22, 2022 From the State Intellectual Property Office of the People's Republic of China Re. Application No. 200880024068.5 (3 pages).
Notice of Violation Unity Requirements Dated Apr. 15, 2021 From the Federal Government Institution, Federal Institute of Industrial Property of the Federal Service of Intellectual Property, Patents and Trademarks of the Russian Federation, FIPS Re. Application No. 2019124280 and Its Translation Into English. (15 Pages).
Notice of Reason(s) for Rejection Dated Aug. 2, 2022 From the Japan Patent Office Re. Application No. 2019-536488 and Its Translation Into English. (7 Pages).
Patent Examination Report Dated Jun. 9, 2022 From the New Zealand Intellectual Property Office Re. Application No. 755725. (4 Pages).
Office Action Dated Oct. 23, 2022 From the Israel Patent Office Re. Application No. 267863. (4 Pages).
Office Action Dated Oct. 24, 2023 From the Israel Patent Office Re. Application No. 267863. (5 Pages).
English Summary Dated Nov. 3, 2023 of Decision on Rejection Dated Oct. 16, 2023 From the State Intellectual Property Office of the People's Republic of China Re. Application No. 201880016068. 5. (1 Page).
Notification of Office Action Dated Jun. 10, 2023 From the State Intellectual Property Office of the People's Republic of China Re. Application No. 201880016068.5. (4 Pages).
Translation Dated Jun. 30, 2023 of Notification of Office Action Dated Jun. 10, 2023 From the State Intellectual Property Office of the People's Republic of China Re. Application No. 201880016068. 5. (3 pages).
Examination Report Dated Jun. 7, 2023 From the Instituto Mexicano de la Propiedad Industrial, Secretaria de Economia, Direccion Divisional de Patentes Re. Application No. MX/a/2019/008076 and Its Translation Into English. (14 Pages).
Grounds of Reason of Rejection Dated May 17, 2023 From the Korean Intellectual Property Office Re. Application No. 10-2019-7023039. (4 Pages).
Decision on Rejection Dated Oct. 16, 2023 From the State Intellectual Property Office of the People's Republic of China Re. Application No. 201880016068.5. (4 Pages).
Grounds of Reason of Rejection Dated Oct. 11, 2023 From the Korean Intellectual Property Office Re. Application No. 10-2019-7023039 (4 Pages).
Informe de Busqueda y Parecer [Search Report and Opinion] Dated Aug. 28, 2023 From the Instituto Nacional de Propiedad Industrial, Ministerio de Economia, Fomento y Turismo, INAPI, Gobierno de Chile Re. Application No. 201901867. and Its Translation Into English (21 Pages).
Translation Dated Jun. 8, 2023 of Grounds of Reason of Rejection Dated May 17, 2023 From the Korean Intellectual Property Office Re. Application No. 10-2019-7023039. (4 Pages).
Machine Translation Dated Oct. 25, 2023 of Decision on Rejection Dated Oct. 16, 2023 From the State Intellectual Property Office of the People's Republic of China Re. Application No. 201880016068. 5. (6 Pages).
Translation Dated Oct. 25, 2023 of Grounds of Reason of Rejection Dated Oct. 11, 2023 From the Korean Intellectual Property Office Re. Application No. 10-2019-7023039 (5 Pages).
Communication Pursuant to Article 94(3) EPC Dated Feb. 12, 2024 From the European Patent Office Re. Application No. 18736643.0 (6 Pages).
Requisition by the Examiner Dated Mar. 14, 2024 From the Innovation, Science and Economic Development Canada, Canadian Intellectual Property Office Re. Application No. 3,048,151. (4 Pages).
Examination Report Dated Jan. 15, 2024 From the Australian Government, IP Australia Re. Application No. 2018205891. (4 Pages).
Notice of Reason(s) for Rejection Dated Dec. 5, 2023 From the Japan Patent Office Re. Application No. 2022-192939 and Its Translation Into English. (8 Pages).
SSIEM "SSIEM 2016 Annual Symposium—Abstracts", Journal of Inherited Metabolic Disease, XP036042342, 39(1): S35-S284, 250 pages, Aug. 12, 2016.
Relatório de Busca e Parecer [Search Report and Opinion] Dated Jul. 2, 09024From the Serviço Público Federal, Ministério da Economia, Instituto Nacional da Propriedade Industrial do Brasil Re. Application No. BR 1120190139206 and Its Machine Translation. (6 Pages).
Examination Report Dated Jun. 4, 2024 From the Australian Government, IP Australia Re. Application No. 2018205891. (2 Pages).
Notice of Reason(s) for Rejection Dated Jun. 11, 2024 From the Japan Patent Office Re. Application No. 2019-536488 and Its Translation Into English. (44 Pages).
Notice of Reason(s) for Rejection Dated Jun. 11, 2024 From the Japan Patent Office Re. Application No. 2022-192939 and Its Translation Into English. (11 Pages).
Kizhner et al. "Characterization of a Chemically Modified Plant Cell Culture Expressed Human α-Galactosidase—A Enzyme for Treatment of Fabry Disease", Molecular Genetics and Metabolism, 114(2): 259-267, Feb. 2015.

* cited by examiner

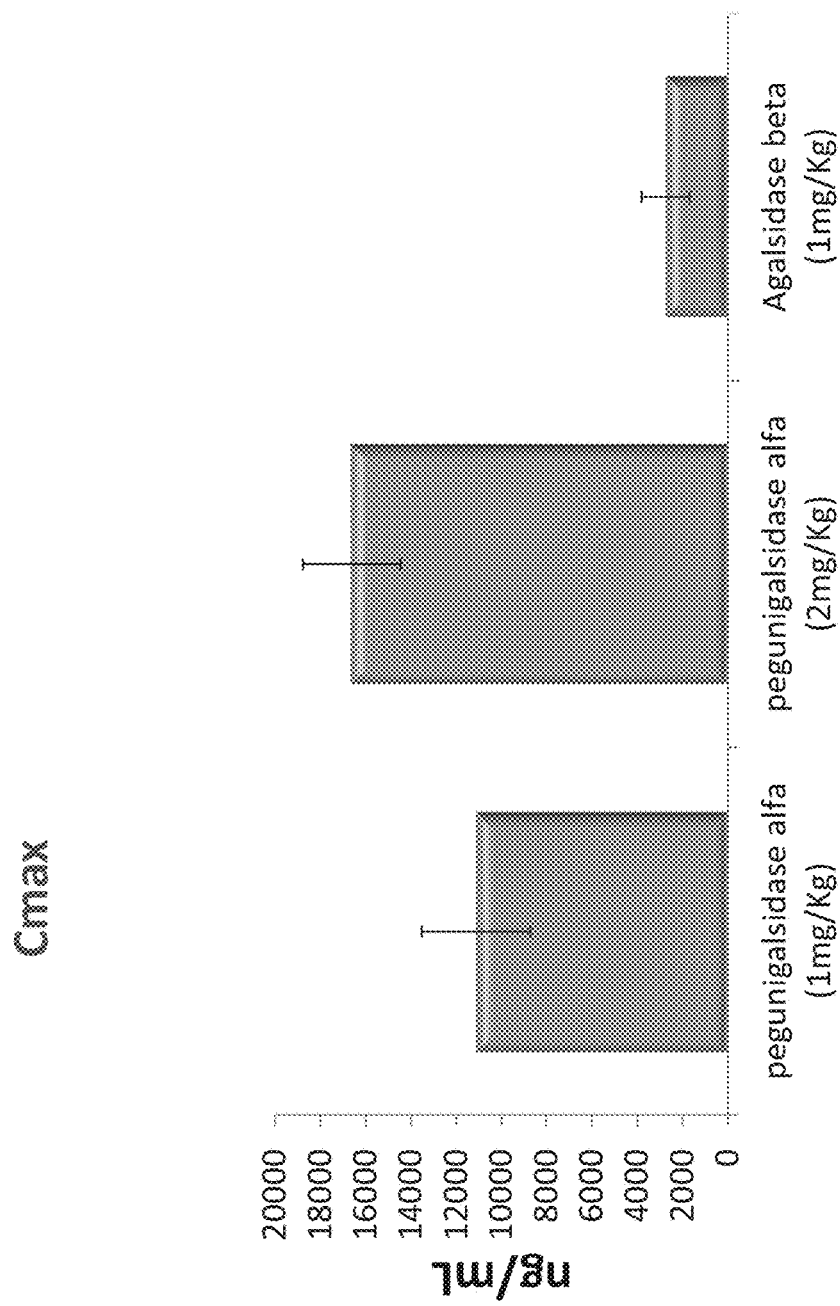

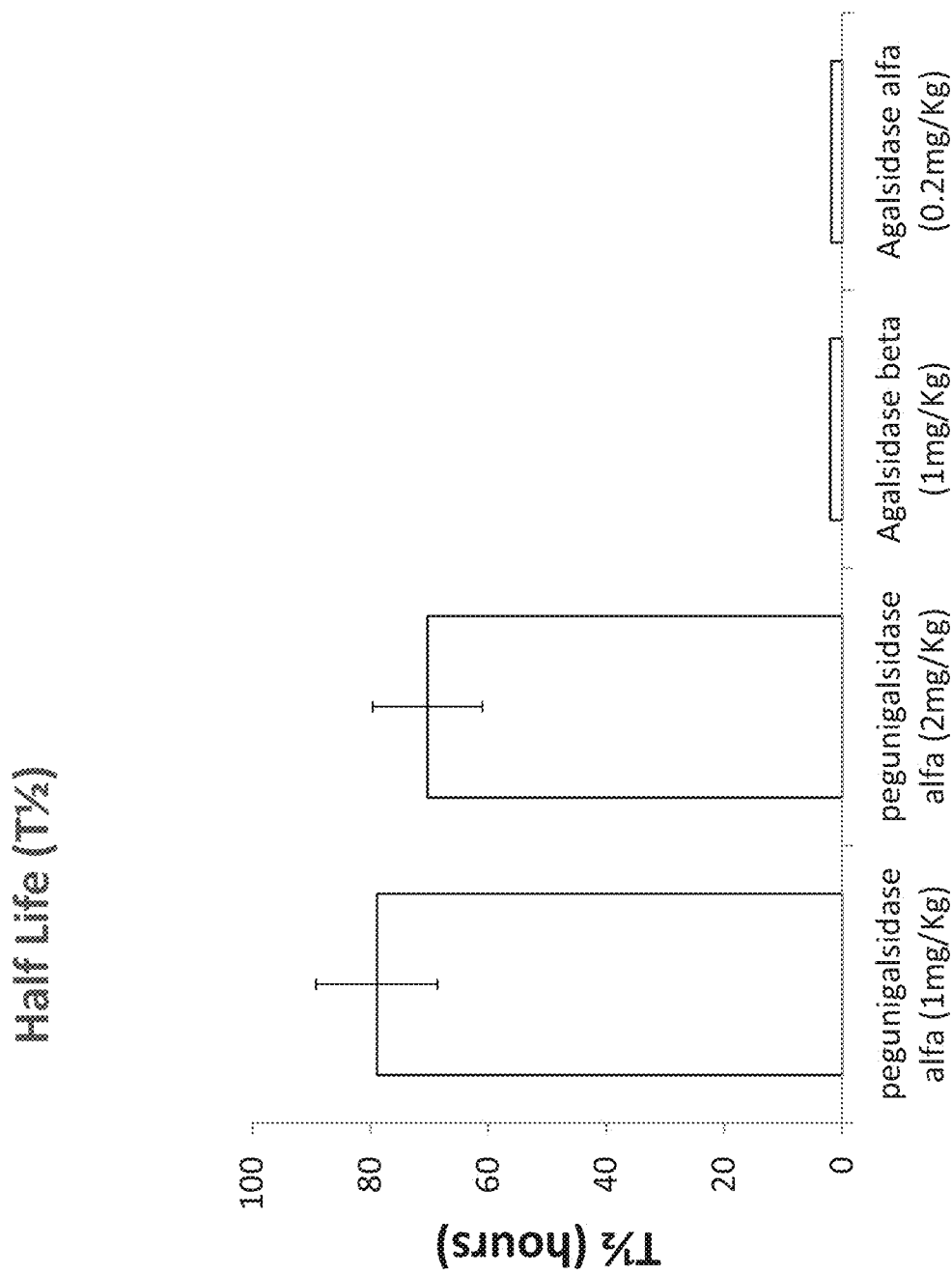

SEQUENCE LISTING

```
<160> NUMBER OF SEQ ID NOS: 3

<210> SEQ ID NO 1
<211> LENGTH: 398
<212> TYPE: PRT
<213> ORGANISM: Homo sapiens
<220> FEATURE:
<221> NAME/KEY: misc_feature
<223> OTHER INFORMATION: Human mature Alpha galactosidase protein
      sequence

<400> SEQUENCE: 1

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175
```

```
Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
    210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
        355                 360                 365

Thr Ser Arg Leu Arg Ser His Ile Asn Pro Thr Gly Thr Val Leu Leu
    370                 375                 380

Gln Leu Glu Asn Thr Met Gln Met Ser Leu Lys Asp Leu Leu
385                 390                 395

<210> SEQ ID NO 2
<211> LENGTH: 405
<212> TYPE: PRT
<213> ORGANISM: Artificial sequence
<220> FEATURE:
<223> OTHER INFORMATION: Recombinant A-Gal mature protein with N'
      terminal G and fused to SEKDEL

<400> SEQUENCE: 2

Gly Leu Asp Asn Gly Leu Ala Arg Thr Pro Thr Met Gly Trp Leu His
1               5                   10                  15

Trp Glu Arg Phe Met Cys Asn Leu Asp Cys Gln Glu Glu Pro Asp Ser
            20                  25                  30

Cys Ile Ser Glu Lys Leu Phe Met Glu Met Ala Glu Leu Met Val Ser
        35                  40                  45

Glu Gly Trp Lys Asp Ala Gly Tyr Glu Tyr Leu Cys Ile Asp Asp Cys
    50                  55                  60

Trp Met Ala Pro Gln Arg Asp Ser Glu Gly Arg Leu Gln Ala Asp Pro
65                  70                  75                  80

Gln Arg Phe Pro His Gly Ile Arg Gln Leu Ala Asn Tyr Val His Ser
                85                  90                  95

Lys Gly Leu Lys Leu Gly Ile Tyr Ala Asp Val Gly Asn Lys Thr Cys
            100                 105                 110

Ala Gly Phe Pro Gly Ser Phe Gly Tyr Tyr Asp Ile Asp Ala Gln Thr
        115                 120                 125

Phe Ala Asp Trp Gly Val Asp Leu Leu Lys Phe Asp Gly Cys Tyr Cys
    130                 135                 140
```

```
Asp Ser Leu Glu Asn Leu Ala Asp Gly Tyr Lys His Met Ser Leu Ala
145                 150                 155                 160

Leu Asn Arg Thr Gly Arg Ser Ile Val Tyr Ser Cys Glu Trp Pro Leu
                165                 170                 175

Tyr Met Trp Pro Phe Gln Lys Pro Asn Tyr Thr Glu Ile Arg Gln Tyr
            180                 185                 190

Cys Asn His Trp Arg Asn Phe Ala Asp Ile Asp Asp Ser Trp Lys Ser
            195                 200                 205

Ile Lys Ser Ile Leu Asp Trp Thr Ser Phe Asn Gln Glu Arg Ile Val
210                 215                 220

Asp Val Ala Gly Pro Gly Gly Trp Asn Asp Pro Asp Met Leu Val Ile
225                 230                 235                 240

Gly Asn Phe Gly Leu Ser Trp Asn Gln Gln Val Thr Gln Met Ala Leu
                245                 250                 255

Trp Ala Ile Met Ala Ala Pro Leu Phe Met Ser Asn Asp Leu Arg His
            260                 265                 270

Ile Ser Pro Gln Ala Lys Ala Leu Leu Gln Asp Lys Asp Val Ile Ala
            275                 280                 285

Ile Asn Gln Asp Pro Leu Gly Lys Gln Gly Tyr Gln Leu Arg Gln Gly
290                 295                 300

Asp Asn Phe Glu Val Trp Glu Arg Pro Leu Ser Gly Leu Ala Trp Ala
305                 310                 315                 320

Val Ala Met Ile Asn Arg Gln Glu Ile Gly Gly Pro Arg Ser Tyr Thr
                325                 330                 335

Ile Ala Val Ala Ser Leu Gly Lys Gly Val Ala Cys Asn Pro Ala Cys
            340                 345                 350

Phe Ile Thr Gln Leu Leu Pro Val Lys Arg Lys Leu Gly Phe Tyr Glu
            355                 360                 365

Trp Thr Ser Arg Leu Arg Ser His Ile Asn Pro Thr Gly Thr Val Leu
            370                 375                 380

Leu Gln Leu Glu Asn Thr Met Gln Met Ser Leu Lys Asp Leu Leu Ser
385                 390                 395                 400

Glu Lys Asp Glu Leu
                405

<210> SEQ ID NO 3
<211> LENGTH: 404
<212> TYPE: PRT
<213> ORGANISM: Artificial sequence
<220> FEATURE:
<223> OTHER INFORMATION: Recombinant A-Gal mature protein fused to
      SEKDEL without N' terminal G

<400> SEQUENCE: 3

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
                20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
        50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
```

-continued

```
                    85                  90                  95
Gly Leu Lys Leu Gly Ile Tyr Ala Asp Val Gly Asn Lys Thr Cys Ala
            100                 105                 110
Gly Phe Pro Gly Ser Phe Gly Tyr Tyr Asp Ile Asp Ala Gln Thr Phe
            115                 120                 125
Ala Asp Trp Gly Val Asp Leu Leu Lys Phe Asp Gly Cys Tyr Cys Asp
            130                 135                 140
Ser Leu Glu Asn Leu Ala Asp Gly Tyr Lys His Met Ser Leu Ala Leu
145                 150                 155                 160
Asn Arg Thr Gly Arg Ser Ile Val Tyr Ser Cys Glu Trp Pro Leu Tyr
            165                 170                 175
Met Trp Pro Phe Gln Lys Pro Asn Tyr Thr Glu Ile Arg Gln Tyr Cys
            180                 185                 190
Asn His Trp Arg Asn Phe Ala Asp Ile Asp Asp Ser Trp Lys Ser Ile
            195                 200                 205
Lys Ser Ile Leu Asp Trp Thr Ser Phe Asn Gln Glu Arg Ile Val Asp
            210                 215                 220
Val Ala Gly Pro Gly Gly Trp Asn Asp Pro Asp Met Leu Val Ile Gly
225                 230                 235                 240
Asn Phe Gly Leu Ser Trp Asn Gln Gln Val Thr Gln Met Ala Leu Trp
            245                 250                 255
Ala Ile Met Ala Ala Pro Leu Phe Met Ser Asn Asp Leu Arg His Ile
            260                 265                 270
Ser Pro Gln Ala Lys Ala Leu Leu Gln Asp Lys Asp Val Ile Ala Ile
            275                 280                 285
Asn Gln Asp Pro Leu Gly Lys Gln Gly Tyr Gln Leu Arg Gln Gly Asp
            290                 295                 300
Asn Phe Glu Val Trp Glu Arg Pro Leu Ser Gly Leu Ala Trp Ala Val
305                 310                 315                 320
Ala Met Ile Asn Arg Gln Glu Ile Gly Gly Pro Arg Ser Tyr Thr Ile
            325                 330                 335
Ala Val Ala Ser Leu Gly Lys Gly Val Ala Cys Asn Pro Ala Cys Phe
            340                 345                 350
Ile Thr Gln Leu Leu Pro Val Lys Arg Lys Leu Gly Phe Tyr Glu Trp
            355                 360                 365
Thr Ser Arg Leu Arg Ser His Ile Asn Pro Thr Gly Thr Val Leu Leu
            370                 375                 380
Gln Leu Glu Asn Thr Met Gln Met Ser Leu Lys Asp Leu Leu Ser Glu
385                 390                 395                 400
Lys Asp Glu Leu
```

THERAPEUTIC REGIMEN FOR THE TREATMENT OF FABRY USING STABILIZED ALPHA-GALACTOSIDASE

RELATED APPLICATIONS

This application is a National Phase of PCT Patent Application No. PCT/IL2018/050018 having International filing date of Jan. 5, 2018, which claims the benefit of priority under 35 USC § 119 (e) of U.S. Provisional Patent Application No. 62/442,537 filed on Jan. 5, 2017. The contents of the above applications are all incorporated by reference as if fully set forth herein in their entirety.

SEQUENCE LISTING STATEMENT

The ASCII file, entitled 78223SequenceListing.txt, created on Jul. 4, 2019, comprising 11,147 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to homodimeric protein structures of α-galactosidase and, particularly, but not exclusively, to effective treatment regimens for treatment of Fabry disease by enzyme replacement therapy with stabilized covalently linked homodimer protein structures of α-galactosidase.

The lysosomal enzyme α-galactosidase-A (α-GAL or α-Gal A; EC 3.2.1.22) catalyzes the removal of galactose from oligosaccharides, glycoproteins and glycolipids during the catabolism of macromolecules. Deficiencies in lysosomal enzymes lead to the accumulation of their substrates in various tissues, conditions known as lysosomal storage diseases. In humans, the absence of functional α-galactosidase-A leads to the accumulation of glycolipids containing terminal α-galactose residues (primarily globotriaosylceramide, which is also referred to as "ceramide trihexoside", "CTH" or "Gb$_3$") in the tissues, leading to Fabry disease. Fabry disease is an X-linked recessive disorder, first described in 1898, characterized by chronic pain, ocular opacities, liver and kidney impairment, skin lesions, vascular deterioration and/or cardiac deficiencies. Recombinant human α-galactosidase-A has the ability to provide and replace the lowered enzyme activity in patients, and enzyme replacement therapy (ERT) using α-GAL was approved in the United States and European countries in 2003 as a treatment for Fabry disease. α-GAL became the second recombinant protein approved for the treatment of a lysosomal storage disorder after β-glucosidase, a treatment for Gaucher disease.

Endogenous and recombinant α-GAL enzymes catalyze the hydrolysis of terminal galactosylated glycolipids in the lysosomes of cells of organs such as the skin, kidneys, heart, etc. This natural action environment is characterized by its acid pH, reaching as low as 4.5. Lysosomal enzymes, including α-GAL, are hence designed to exert their maximal activity at these low pH levels.

Current Fabry ERT treatments are based on mammalian-cell derived recombinant α-GAL which is considered to be of limited clinical efficacy and currently not offering a satisfactory clinical solution for Fabry patients.

X-ray structure analysis reveals that human α-GAL is a homodimeric glycoprotein with each monomer composed of two domains, a $(\beta/\alpha)_8$ domain containing the active site and a C-terminal domain containing eight antiparallel β strands on two sheets in a β sandwich [Garman & Garboczi, *J Mol Biol* 2004, 337:319-335].

Both structural (X-ray crystallography) and biochemical (kinetic) evidence suggest active site cooperativity between the monomer units of the homodimeric structure, stressing the importance of dimerization for enzymatic activity and stability of therapeutic α-GAL compositions.

WO 2009/024977, by the present assignee, which is incorporated by reference as if fully set forth herein, teaches conjugates of a saccharide and a biomolecule, covalently linked therebetween via a non-hydrophobic linker, as well as medical uses utilizing such conjugates.

WO2011/061736, by the present assignee, which is incorporated by reference as if fully set forth herein teaches methodologies which utilize α-galactosidase which exhibits a lysosomal activity at pH levels higher than lysosomal pH.

WO2011/107990, by the present assignee, which is incorporated by reference as if fully set forth herein teaches a covalently linked multimeric protein structure comprising at least two α-galactosidase monomers, having robust α-galactosidase catalytic activity under physiological conditions and enhanced pharmacodynamics, and suggestions for therapeutic uses thereof.

WO2012/098537, by the present assignee, which is incorporated by reference as if fully set forth herein, teaches nucleic acid constructs for recombinant expression of a catalytically active α-galactosidase in plants, and suggestions for the therapeutic use thereof.

Additional background art include Bendele et al. [*Toxicological Sciences* 1998, 42:152-157], U.S. Pat. Nos. 5,256,804, 5,580,757 and 5,766,897, International Patent Application PCT/NL2007/050684 (published as WO 2008/075957), US Patent Publication US20160184409 to Treco et al, and Seely & Richey [*J Chromatography A* 2001, 908: 235-241].

SUMMARY OF THE INVENTION

According to an aspect of some embodiments of the present invention, there is provided a method of treating Fabry disease in a human subject in need thereof, the method comprising administering to the subject a therapeutically effective amount of recombinant human α-galactosidase, wherein the therapeutically effective amount of the recombinant human α-galactosidase is 0.2-2.0 mg/Kg, thereby treating Fabry disease in the subject, wherein the administering is effected in intervals of greater than two weeks and wherein monomers of the recombinant human α-galactosidase are covalently linked to one another via a linking moiety of 20-600 atoms in length.

According to an aspect of some embodiments of the present invention, there is provided a method of treating Fabry disease in a human subject in need thereof, the method comprising administering to the subject a therapeutically effective amount of recombinant human α-galactosidase, wherein the therapeutically effective amount of the recombinant human α-galactosidase is 0.2-2.0 mg/Kg, thereby treating Fabry disease in the subject, wherein the administering is effected in intervals of greater than two weeks to every 4 weeks and wherein monomers of the recombinant human α-galactosidase are covalently linked to one another via a linking moiety of 20-600 atoms in length.

According to an aspect of some embodiments of the present invention the recombinant human α-galactosidase is a plant recombinant human α-galactosidase.

According to an aspect of some embodiments of the present invention the plant recombinant human α-galactosidase is cross-linked with bis-NHS-PEG$_{45}$.

According to an aspect of some embodiments of the present invention the intervals are three weeks or four weeks.

According to an aspect of some embodiments of the present invention the intervals are 17 days to 8 weeks.

According to an aspect of some embodiments of the present invention the intervals are 17 days to 6 weeks.

According to an aspect of some embodiments of the present invention the intervals are 17 days to 5 weeks.

According to an aspect of some embodiments of the present invention the intervals are 3 weeks to 6 weeks.

According to an aspect of some embodiments of the present invention the intervals are 3 weeks to 5 weeks.

According to an aspect of some embodiments of the present invention the intervals are 3 weeks to 4 weeks.

According to an aspect of some embodiments of the present invention the intervals are 4 weeks to 6 weeks.

According to an aspect of some embodiments of the present invention the intervals are 4 weeks to 5 weeks.

According to an aspect of some embodiments of the present invention the administering is intravenous administration.

According to an aspect of some embodiments of the present invention the administering is effected at a dose of 1.0 mg/Kg.

According to an aspect of some embodiments of the present invention the administering is effected at a dose of 2.0 mg/Kg.

According to an aspect of some embodiments of the present invention the administering is effected once every three weeks.

According to an aspect of some embodiments of the present invention the administering is effected once every four weeks.

According to an aspect of some embodiments of the present invention the administering is effected once every five weeks.

According to an aspect of some embodiments of the present invention the administering is effected once every six weeks.

According to an aspect of some embodiments of the present invention the therapeutically effective amount of recombinant human α-galactosidase reduces Gb3 and/or lyso Gb3 in the subject.

According to an aspect of some embodiments of the present invention the therapeutically effective amount of recombinant human α-galactosidase maintains stability or attenuates deterioration of cardiac parameters in the subject.

According to an aspect of some embodiments of the present invention the cardiac parameters are LVM or LVMI, measured by MRI compared to pre-treatment values.

According to an aspect of some embodiments of the present invention the therapeutically effective amount of recombinant human α-galactosidase maintains stability of reduction of plasma Gb3 and/or lyso-Gb3 concentrations in the subject.

According to an aspect of some embodiments of the present invention the therapeutically effective amount of recombinant human α-galactosidase maintains stability of reduction of urine Gb3 concentrations in the subject.

According to an aspect of some embodiments of the present invention the therapeutically effective amount of recombinant human α-galactosidase attenuates Fabry disease-related deterioration of kidney function in the subject.

According to an aspect of some embodiments of the present invention the therapeutically effective amount of recombinant human α-galactosidase maintains stability of kidney function in the subject.

According to an aspect of some embodiments of the present invention the therapeutically effective amount of recombinant human α-galactosidase maintains stability of, or attenuates deterioration of at least one gastrointestinal parameter in the subject.

According to an aspect of some embodiments of the present invention the gastrointestinal parameter is abdominal pain and/or frequency of abdominal pain, measured after 6 months treatment, compared to pre-treatment values.

According to an aspect of some embodiments of the present invention the therapeutically effective amount of recombinant human α-galactosidase maintains stability or attenuates deterioration of the Mainz Severity Score Index (MSSI) in the subject.

According to an aspect of some embodiments of the present invention the reduction in MSSI is measured after 6 months treatment, compared to pre-treatment values.

According to an aspect of some embodiments of the present invention the recombinant human α-galactosidase has a circulating half-life ($T_{1/2}$) of at least 5 hours following administration.

According to an aspect of some embodiments of the present invention the recombinant human α-galactosidase has a circulating half-life ($T_{1/2}$) of at least 20 hours following administration.

According to an aspect of some embodiments of the present invention the recombinant human α-galactosidase has a circulating half-life ($T_{1/2}$) of at least 50 hours following administration.

According to an aspect of some embodiments of the present invention the recombinant human α-galactosidase has a $C_{max}$ of at least 5000 ng/ml following administration of 1 mg/Kg of the recombinant human α-galactosidase.

According to an aspect of some embodiments of the present invention the recombinant human α-galactosidase has a $C_{max}$ of at least 8000 ng/ml following administration of 2 mg/Kg.

According to an aspect of some embodiments of the present invention the recombinant human α-galactosidase has a bioavailability ($AUC_{0-\infty}$) of at least 100,000 ng*hr/ml following administration of 1.0 mg/Kg of the recombinant human α-galactosidase.

According to an aspect of some embodiments of the present invention the recombinant human α-galactosidase has a bioavailability ($AUC_{0-\infty}$) of at least 400,000 ng*hr/ml following administration of 2.0 mg/Kg of the recombinant human α-galactosidase.

According to an aspect of some embodiments of the present invention, there is provided a unit dosage form comprising 2.0-500 mg recombinant human α-galactosidase formulated for administration to a human subject.

According to an aspect of some embodiments of the present invention the unit dosage form comprises 10 mg recombinant human α-galactosidase.

According to an aspect of some embodiments of the present invention the unit dosage form comprises 50 mg plant recombinant human α-galactosidase.

According to an aspect of some embodiments of the present invention the unit dosage form comprises 100-180 mg recombinant human α-galactosidase.

According to an aspect of some embodiments of the present invention the unit dosage form comprises 150 mg recombinant human α-galactosidase.

According to an aspect of some embodiments of the present invention the unit dosage form is formulated as a liquid.

According to an aspect of some embodiments of the present invention the unit dosage form is formulated for intravenous administration.

According to an aspect of some embodiments of the present invention monomers of the recombinant human α-galactosidase are covalently linked to one another via a poly(alkylene) glycol linking moiety.

According to an aspect of some embodiments of the present invention the poly(alkylene) glycol linking moiety comprises at least 20 alkylene groups.

According to an aspect of some embodiments of the present invention the recombinant human α-galactosidase is a plant recombinant human α-galactosidase.

According to an aspect of some embodiments of the present invention the plant recombinant human α-galactosidase is plant recombinant human α-galactosidase cross-linked with bis-NHS-PEG$_{45}$.

According to an aspect of some embodiments of the present invention the recombinant human α-galactosidase comprises a human α-galactosidase protein having an amino acid sequence as set forth in any one of SEQ ID NOs: 1-3.

According to an aspect of some embodiments of the present invention the human α-galactosidase protein is as set forth in SEQ ID NO: 2 or 3.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-3C are histograms illustrating the pharmacokinetic parameters of pegunigalsidase alfa, expressed as maximal plasma concentration ($C_{max}$, in ng/mL) (FIG. 3A), half-life (T ½, in hours) (FIG. 3B) and calculated total available enzyme (area under the curve, $AUC_{0-\infty}$, in ug*min/mL) (FIG. 3C), compared with that of available, published data of Agalsidase beta (r-alphahGalA, Fabrazyme™) and Agalsidase alfa (Replagal™, Shire Human Genetic Therapies (HGT), Inc., Cambridge, MA). Dosages of pegunigalsidase alfa represented are 1.0 and 2.0 mg/Kg, dosage of Agalsidase beta 1.0 mg/Kg and of Agalsidase alfa 0.2 mg/Kg. Note the higher pharmacokinetics, in all parameters ($C_{max}$; $T_{1/2}$ and $AUC_{0-\infty}$), of pegunigalsidase alfa, compared to Agalsidase alfa or beta;

FIG. 4A is a schematic illustration representing the extrapolated enzyme availability, over a four week period following the single infusion;

FIG. 4B is a modeling of comparisons between pharmacokinetic parameters of 2 mg/kg pegunigalsidase alfa given once within a 4 week interval and 1 mg/Kg agalsidase beta (Fabrazyme) given twice over the same 4 week interval;

FIG. 4B represents the comparison of 4 week enzyme availability (partial AUC calculated per sequential week) for 2 mg/Kg pegunigalsidase alfa administered once every 4 weeks with the partial AUC of 1 mg/Kg agalsidase beta (Fabrazyme) administered once every 2 weeks. Note the virtual absence of partial AUC of agalsidase beta enzyme in the week following administration (see agalsidase beta weeks 2 and 4), compared to the projected significant enzyme availability following single administration of pegunigalsidase alfa throughout the entire 4 weeks following administration.

DESCRIPTION OF SPECIFIC EMBODIMENTS OF THE INVENTION

Figure 1:
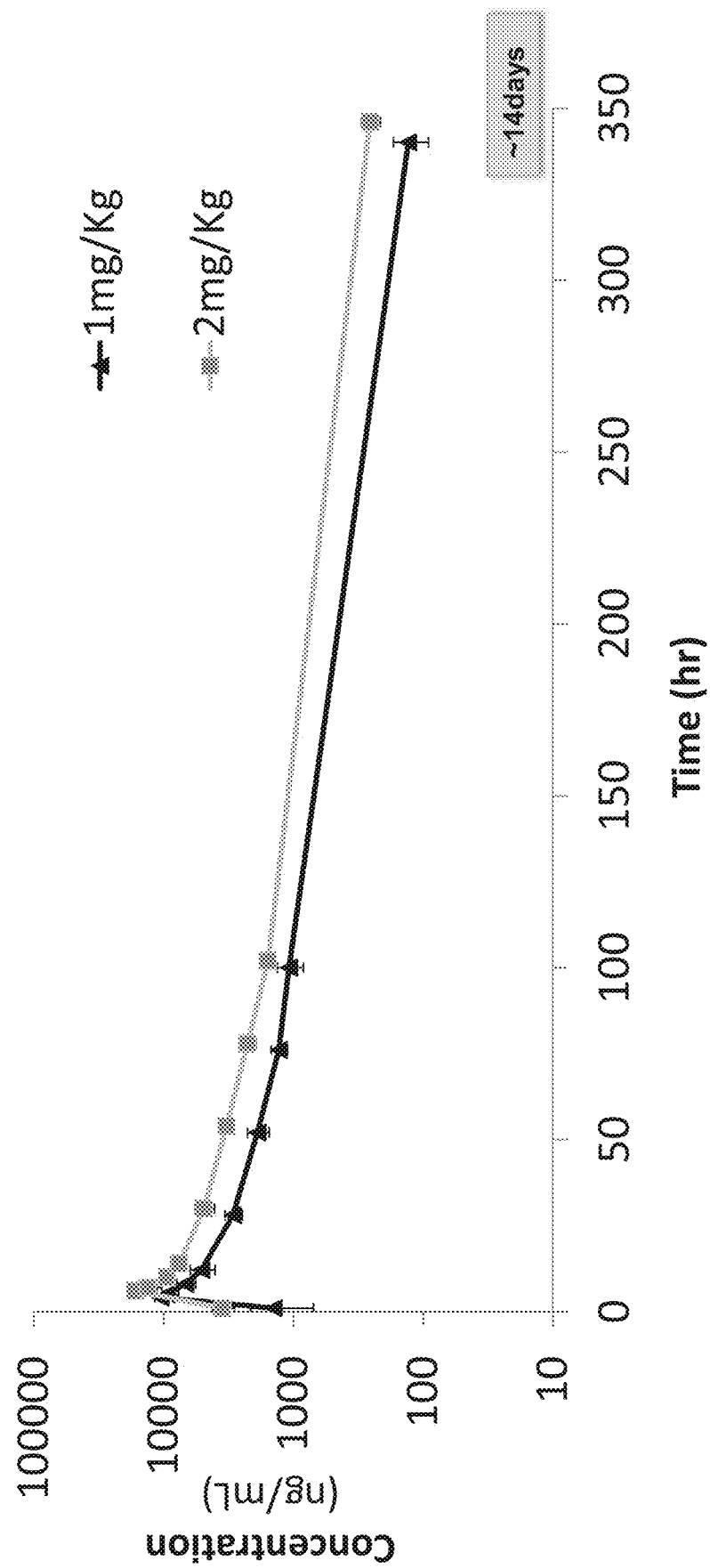
FIG. 1 is a graph showing the pharmacokinetic profile of plant recombinant human α-GAL cross-linked with bis-NHS-PEG$_{45}$ (pegunigalsidase alfa), measured in plasma of patients up to 14 days post administration, at the start of the treatment (Day 1), expressed as nanogram (ng) pegunigalsidase alfa per milliliter (ml) plasma. Enzyme concentration was measured in blood samples drawn at 0 hr (pre-administration/infusion), 1 hr (1 hour after initiation of the administration), at the end of the administration (infusion) (EOI) and 1, 4, 8, 24, 48, 72, 96 hours after the EOI, and 2 weeks (14 days) after administration ("$C_{2wk}$") before subsequent administration of the pegunigalsidase alfa. The graph represents average plasma values (ng/ml) for all cohorts at the different sampling times over the 14 day period, on a logarithmic scale. Triangles (light grey line) represent a dose of 1.0 mg/Kg and squares (black line) 2.0 mg/Kg pegunigalsidase alfa.

The present invention, in some embodiments thereof, relates to a stabilized covalently linked human alpha galactosidase homodimer enzyme and, more particularly, but not exclusively, to a stabilized, covalently linked plant recombinant human alpha galactosidase enzyme, effective treatment regimens for uses thereof in treating Fabry disease in human subjects by enzyme replacement therapy.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Deficiencies of a lysosomal protein (e.g., defects in a lysosomal protein or absence of a lysosomal protein) can cause considerable harm to the health of a subject (a lysosomal storage disease). Enzyme replacement therapy (ERT), in which the deficient protein is administered to a patient, has been used in attempts to treat lysosomal storage diseases. However, administration of the deficient protein does not necessarily result in a considerable and/or persistent activity of the administered protein in vivo.

Fabry disease is an example of an X-linked recessive (inherited) lysosomal storage disease which can cause a wide range of symptoms. A deficiency of the lysosomal enzyme α-galactosidase A due to mutations causes a glycolipid known as globotriaosylceramide (also known as $Gb_3$ or ceramide trihexoside) to accumulate within the blood vessels, other tissues, and organs. This accumulation leads to an impairment of their proper function. Two enzyme replacement therapies (ERTs) are available to functionally compensate for α-galactosidase deficiency. Agalsidase alfa (Replagal®, Shire) and agalsidase beta (Fabrazyme®, Genzyme-Sanofi) are both recombinant forms of the human α-galactosidase A enzyme. Both agalsidase alfa and agalsidase beta suffer from short half-life which leads to limited bioavailability resulting in an unsatisfactory clinical outcome.

Motivated by a need to solve the compromised activity of α-galactosidases, stabilized forms of α-galactosidase (α-GAL) were developed, which exhibited enhanced activity and/or a longer lasting activity under both lysosomal conditions and in a serum environment, indicating potential long lasting enhanced activity of the protein in vivo, under clinically relevant conditions. Furthermore, the covalently linked human α-galactosidase of the invention exhibited enhanced activity and/or a longer lasting activity in serum from Fabry patients.

Using the stabilized covalently linked human α-galactosidase of the invention, the present inventors have developed effective novel therapeutic dose and regimens for enzyme replacement therapy of Fabry disease in humans. Clinical experience with the stabilized covalently linked human α-galactosidase of the invention has shown that ERT with the stabilized covalently linked human α-galactosidase of the invention, according to the novel therapeutic regimens, is safe and effective for treatment of Fabry disease in humans. The stabilized covalently linked human α-galactosidase of the invention exhibited greatly enhanced pharmacokinetics, maintaining plasma concentrations for greater than 10 days post administration, $C_{max}$ of greater than 5,000 ng/ml with 1.0 mg/Kg dose (7,900-23,000 ng/mL) and greater than 8,000 ng/ml with 2.0 mg/Kg dose (13,900-46,500 ng/mL), and enhanced bioavailability (AUC) compared to currently available ERTs.

Treatment with the stabilized covalently linked human α-galactosidase of the invention reduced renal peritubular capillary ceramidase trihexoside inclusions significantly attenuated the characteristic deterioration in kidney function, improved kidney function and gastrointestinal symptoms, reduced patient's pain index scores, improved or stabilized patient's cardiac functions, and improved physical activity and overall quality of life. Clinical improvement such as observed in the clinical studies, with an effective 2 mg/kg dosage regimen using wider infusion intervals due to the improved pharmacokinetics and bioavailability of the stabilized covalently linked human α-galactosidase of the invention can provide ERT coverage to specific Fabry population such as but not limited to mild to moderate, young, early diagnosed and/or steady patients, therefore offering greater convenience of therapy and patient compliance while managing the patient's symptoms, leading to significant improvement in patient's quality of life and delayed risk of disease complications.

Hence, according to an aspect of some embodiments of the present invention there is provided a method of treating Fabry disease in a human subject in need thereof, the method comprising administering to the subject a therapeutically effective amount of covalently linked plant recombinant human α-galactosidase, wherein said therapeutically effective amount of said covalently linked plant recombinant human α-galactosidase is 0.2-2.0 mg/kg, thereby treating Fabry disease in the subject, wherein said administering is effected in intervals of greater than two weeks to every 4 weeks and wherein the monomers of said covalently linked plant recombinant human α-galactosidase are covalently linked to one another via a poly(alkylene) glycol linking moiety.

According to some embodiments, the covalently linked plant recombinant human α-galactosidase is a covalently linked homodimer plant recombinant human α-galactosidase.

According to some embodiments, the covalently linked homodimer plant recombinant human alpha galactosidase protein features a stability higher than that of native α-galactosidase and/or an initial activity higher than that of native α-galactosidase, as described in detail below. In some embodiments, the stabilized covalently linked human α-galactosidase protein is a plant recombinant human α-GAL cross-linked with bis-NHS-$PEG_{45}$.

It will be noted that in some embodiments, the method can be effected using stabilized covalently linked human α-galactosidase protein comprising a recombinant human α-galactosidase protein derived from non-plant (e.g. mammalian) cells, such as commercially available Agalsidase alfa (Replagal®, Shire) and agalsidase beta (Fabrazyme®, Genzyme), recombinant alpha galactosidase produced in non-mammalian cells (plant, bacteria, insect, fungi, etc) or suitable alpha galactosidase of any other origin.

As used herein, "Fabry disease" refers to any alpha-galactosidase A deficiency. "Alpha galactose A deficiency" refers to any deficiency in the natural activity of alpha-galactosidase A in a patient, resulting in abnormal accumulations of glycolipids (e.g., globotriaosylceramide) primarily in capillary endothelial cells, renal cells and/or cardiac myocytes. The deposits of this material can result in severe neuropathic pain (e.g., acroparesthesia and lacerative pain), serious renal and cardiovascular disease, and/or stroke. The glycolipid accumulation may induce severe symptoms as typically observed in individuals who are suffering from Fabry disease. Generally, more severe symptoms are observed in male patients but can also be seen in heterozygous female carriers of the defective gene. The disease is known to be underdiagnosed, especially in female patients. Affected individuals have a greatly shortened life expectancy; death usually results from renal, cardiac, and/or cerebrovascular complications at approximately the fourth and fifth decade in life.

Herein, the term "monomer" with respect to α-galactosidase refers to an individual polypeptide "subunit" of α-galactosidase. The polypeptide may include non-peptidic substituents (e.g., one or more saccharide moieties).

Herein, the term "native" with respect to α-galactosidase encompasses proteins comprising an amino acid sequence substantially identical (i.e., at least 95% homology, optionally at least 95% identity, optionally at least 99% homology, optionally at least 99% identity and optionally 100% identity) to an amino acid sequence of a naturally occurring α-galactosidase protein. A native α-galactosidase may be a protein isolated from a natural source, or a recombinantly produced protein (e.g., derived from human cells, mammalian cells, plant cells, yeast cells, bacterial cells, insect cells and the like).

The term "native", when used in reference to a quaternary structure of α-galactosidase (e.g., an α-galactosidase dimer), further comprises a quaternary structure substantially identical to that of a naturally occurring protein.

Herein, the phrase "naturally occurring protein" refers to a protein in a form which occurs in nature (e.g., in an organism), with respect to the protein's amino acid sequence, as well as the protein's quaternary structure if the protein is in a stabilized, homodimeric form.

Post-translational modifications (e.g., glycosylation) of naturally occurring α-galactosidase proteins (e.g., in an organism which expresses the naturally occurring α-galactosidase protein) may be present, absent or modified in the native form of α-galactosidase referred to herein. A native form of α-galactosidase (e.g., a recombinantly produced α-galactosidase) may optionally comprise different post-translational modifications than those of the naturally occurring α-galactosidase, provided that the native form of the α-galactosidase retains a substantially similar amino acid sequence and structure as the naturally occurring α-galactosidase, as described hereinabove.

Herein, the native form of a protein may refer to a monomeric structure (e.g., an α-galactosidase monomer) and/or a multimeric structure (e.g., an α-galactosidase dimer). For example, a dimeric protein can be described as a native form of α-galactosidase, and a monomeric polypeptide in a dimeric protein can be described as a native form of the α-galactosidase monomer.

Optionally, the multimeric protein structure described herein is a dimeric structure, as is the native form of α-galactosidase.

Alternatively, the stabilized covalently linked human α-galactosidase of the invention comprises more than two α-galactosidase monomers. For example, the multimeric protein structure may be a tetramer, a hexamer, or an octamer comprised of α-galactosidase monomers.

The stabilized covalently linked human α-galactosidase of the invention described herein comprises covalent bonds which link the α-galactosidase monomers therein, and which are absent from the native form of the α-galactosidase.

Thus, for example, the linking moiety is optionally a moiety which is covalently attached to a side chain, an N-terminus or a C-terminus, or a moiety related to post-translational modifications (e.g., a saccharide moiety) of an α-galactosidase monomer, as well as to a side chain, an N-terminus or a C-terminus, or a moiety related to post-translational modifications (e.g., a saccharide moiety) of another α-galactosidase monomer. Exemplary such linking moieties are described in detail hereinunder.

Optionally, the linking moiety is devoid of a disulfide bond. However, a linking moiety which includes a disulfide bond at a position which does not form a link between monomers (e.g., cleavage of the disulfide bond does not cleave the link between the monomers) is within the scope of this embodiment of the invention. A potential advantage of linking moiety devoid of a disulfide bond is that it is not susceptible to cleavage by mildly reducing conditions, as are disulfide bonds.

The linking moiety is also referred to herein as a cross-linking moiety. The linking of α-galactosidase monomers by a linking moiety is referred to herein as "cross-linking".

In some embodiments, relatively short linking moieties may be less effective than longer linking moieties at cross-linking between different α-galactosidase monomers.

Hence, according to some embodiments, the linking moiety is not a covalent bond, a chemical atom or group, but is rather a bridging moiety.

Hence, according to some embodiments, the linking moiety is at least 10 atoms long, optionally at least 20 atoms long, optionally at least 30 atoms long, optionally at least 50 atoms long, optionally at least 100 atoms long, optionally at least 200 atoms long, optionally at least 300 atoms long, optionally at least 400 atoms long, optionally at least 500 atoms long, optionally at least 600 atoms long, optionally at least 700 atoms long, optionally at least 800 atoms long and optionally at least 1000 atoms long. In some embodiments, the length of the linking moiety (in number of atoms) is in the range of 10-1000 atoms, 15-800 atoms, 20-600 atoms, 50-500 atoms, 65-400 atoms, 75-350 atoms and 80-200 atoms. In specific embodiments, the length of the linking moiety (in number of atoms) is 20-600 atoms. In another specific embodiment, the length of the linking moiety (in number of atoms) is 140 atoms.

Herein, the length of a linking moiety (when expressed as a number of atoms) refers to length of the backbone of the linking moiety, i.e., the number atoms forming a linear chain between residues of each of two monomers linked via the linking moiety.

According to some aspects of the invention, monomers of the stabilized covalently linked human α-galactosidase of the invention are covalently linked to one another via a poly(alkylene) glycol linking moiety, e.g. in some embodiments, the linking moiety comprises a poly(alkylene glycol) chain.

The phrase "poly(alkylene glycol)", as used herein, encompasses a family of polyether polymers which share the following general formula: —O—[(CH$_2$)$_m$—O—]$_n$—, wherein m represents the number of methylene groups present in each alkylene glycol unit, and n represents the number of repeating units, and therefore represents the size or length of the polymer. For example, when m=2, the polymer is referred to as a polyethylene glycol, and when m=3, the polymer is referred to as a polypropylene glycol.

In some embodiments, m is an integer greater than 1 (e.g., m=2, 3, 4, etc.).

Optionally, m varies among the units of the poly(alkylene glycol) chain. For example, a poly(alkylene glycol) chain may comprise both ethylene glycol (m=2) and propylene glycol (m=3) units linked together.

The poly(alkylene glycol) optionally comprises at least two functional groups (e.g., as described herein), each functional group forming a covalent bond with one of the α-galactosidase monomers. The functional groups are optionally terminal groups of the poly(alkylene glycol), such that the entire length of the poly(alkylene glycol) lies between the two functional groups.

The phrase "poly(alkylene glycol)" also encompasses analogs thereof, in which the oxygen atom is replaced by another heteroatom such as, for example, S, —NH— and the like. This term further encompasses derivatives of the above, in which one or more of the methylene groups composing the polymer are substituted. Exemplary substituents on the methylene groups include, but are not limited to, alkyl, cycloalkyl, alkenyl, alkynyl, alkoxy, hydroxy, oxo, thiol and thioalkoxy, and the like.

The phrase "alkylene glycol unit", as used herein, encompasses a —$(CH_2)_m$—O— group or an analog thereof, as described hereinabove, which forms the backbone chain of the poly(alkylene glycol), wherein the $(CH_2)_m$ (or analog thereof) is bound to a heteroatom belonging to another alkylene glycol unit or to an α-galactosidase monomer moiety (in cases of a terminal unit), and the O (or heteroatom analog thereof) is bound to the $(CH_2)_m$ (or analog thereof) of another alkylene glycol unit, or to a functional group which forms a bond with an α-galactosidase monomer.

An alkylene glycol unit may be branched, such that it is linked to 3 or more neighboring alkylene glycol units, wherein each of the 3 or more neighboring alkylene glycol units are part of a poly(alkylene glycol) chain. Such a branched alkylene glycol unit is linked via the heteroatom thereof to one neighboring alkylene glycol unit, and heteroatoms of the remaining neighboring alkylene glycol units are each linked to a carbon atom of the branched alkylene glycol unit. In addition, a heteroatom (e.g., nitrogen) may bind more than one carbon atom of an alkylene glycol unit of which it is part, thereby forming a branched alkylene glycol unit (e.g., $[(-CH_2)_m]_2N$— and the like).

In exemplary embodiments, at least 50% of alkylene glycol units are identical, e.g., they comprise the same heteroatoms and the same m values as one another. Optionally, at least 70%, optionally at least 90%, and optionally 100% of the alkylene glycol units are identical. In exemplary embodiments, the heteroatoms bound to the identical alkylene glycol units are oxygen atoms. In further exemplary embodiments, m is 2 for the identical units.

In one embodiment, the linker is a single, straight chain linker, for example, polyethylene glycol (PEG).

As used herein, the term "poly(ethylene glycol)" describes a poly(alkylene glycol), as defined hereinabove, wherein at least 50%, at least 70%, at least 90%, and preferably 100%, of the alkylene glycol units are —$CH_2CH_2$—O—. Similarly, the phrase "ethylene glycol units" is defined herein as units of —$CH_2CH_2O$—.

According to optional embodiments, the linking moiety comprises a poly(ethylene glycol) or analog thereof, having a general formula:

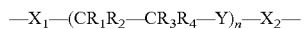

—$X_1$—$(CR_1R_2$—$CR_3R_4$—$Y)_n$—$X_2$— wherein each of $X_1$ and $X_2$ is a functional group (e.g., as described herein) that forms a covalent bond with at least one α-galactosidase monomer;

Y is O, S or $NR_5$ (optionally O);

n is an integer, optionally from 1 to 200 (optionally from 5 to 150, and optionally from 40 to 70), although higher values of n are also contemplated; and each of $R_1$, $R_2$, $R_3$, $R_4$, and $R_5$ is independently selected from the group consisting of hydrogen, alkyl, cycloalkyl, alkenyl, alkynyl, alkoxy, hydroxy, oxo, thiol and thioalkoxy.

In some embodiments, n is at least 5, optionally at least 8, optionally at least 15, optionally at least 25, and optionally at least 40.

In some embodiments, n is no more than 200, optionally no more than 150, and optionally no more than 70.

The poly(ethylene glycol) or analog thereof may optionally comprise a copolymer, for example, wherein the $CR_1R_2$—$CR_3R_4$—Y units in the above formula are not all identical to one another.

In some embodiments, at least 50% of $CR_1R_2$—$CR_3R_4$—Y units are identical. Optionally, at least 70%, optionally at least 90%, and optionally 100% of the $CR_1R_2$—$CR_3R_4$—Y units are identical.

Optionally, the linking moiety is branched, for example, such that for one or more $CR_1R_2$—$CR_3R_4$—Y units in the above formula, at least of one of $R_1$, $R_2$, $R_3$, $R_4$, and $R_5$ is —$(CR_1R_2$—$CR_3R_4$—$Y)_p$—$X_3$—, wherein $R_1$-$R_4$ and Y are as defined hereinabove, p is an integer as defined herein for n (e.g., from 1 to 200), and $X_3$ is as defined herein for $X_1$ and $X_2$.

The functional groups may optionally form a bond such as, but not limited to, an amide bond, an amine bond, an ester bond, and/or an ether bond.

For example, the functional group may optionally comprise a carbonyl group which forms an amide bond with a nitrogen atom in a polypeptide (e.g., in a lysine residue or N-terminus), or an ester bond with an oxygen atom in a polypeptide (e.g., in a serine, threonine or tyrosine residue).

Alternatively or additionally, the functional group may optionally comprise a heteroatom (e.g., N, S, O) which forms an amide bond, ester bond or thioester bond with a carbonyl group in a polypeptide (e.g., in a glutamate or aspartate residue or in a C-terminus).

Alternative or additionally, the functional group may comprise an alkyl or aryl group attached to a polypeptide (e.g., to a heteroatom in the polypeptide).

Alternatively or additionally, the functional group may optionally comprise a nitrogen atom which forms an amine bond with an alkyl group in an α-galactosidase monomer, or an α-galactosidase monomer may optionally comprise a nitrogen atom which forms an amine bond with an alkyl group in the functional group. Such an amine bond may be formed by reductive amination (e.g., as described hereinbelow).

In some embodiments, at least one of the functional groups forms an amide bond with a polypeptide (e.g., with a lysine residue therein).

The functional groups may be identical to one another or different.

In some embodiments, at least one of the functional groups is attached to one functionality of a polypeptide (e.g., an amine group of a lysine residue or N-terminus), and at least one of the functional groups is attached to a different functionality of a polypeptide (e.g., a thiol group of a cysteine residue).

In some embodiments, the stabilized covalently linked human α-galactosidase may contain additional PEG moieties bound to only a single subunit through binding to a lysine residue in that subunit.

In some embodiments, the stabilized covalently linked human α-galactosidase of the invention is cross-linked with bis-NHS-$PEG_{45}$. The production and characteristics of such a plant recombinant human α-galactosidase cross-linked with bis-NHS-$PEG_{45}$ suitable for use in the instant invention is described in detail in PCT Application WO2011/107990, by the present assignee. The stabilized, covalently linked plant recombinant human α-galactosidase cross-linked with bis-NHS-$PEG_{45}$ described herein is also referred to herein as pegunigalsidase alfa.

The stabilized, covalently linked plant recombinant human α-galactosidase cross-linked with bis-NHS-$PEG_{45}$ described herein is biologically active, having α-galactosidase activity. The α-galactosidase activity described herein is a biological activity which is characteristic of α-galactosidase (e.g., a catalytic activity characteristic of α-galactosidase, such as hydrolysis of a terminal α-galactosyl moiety of a substrate).

In some embodiments, a catalytic activity of α-galactosidase is characterized by a rate of catalysis at saturation (i.e., a $V_{max}$ value).

Alternatively, the α-galactosidase activity is a therapeutic activity (e.g., an enzymatic activity having a therapeutic effect), such as a therapeutic activity in the context of Fabry disease. Optionally, the therapeutic activity is determined in experimental animals (e.g., Fabry mice), and optionally in human Fabry patients.

Techniques for determining an activity of α-galactosidase will be known to a skilled person. Typically, the α-galactosidase (i.e., the native form or a multimeric protein structure described herein) is contacted with a compound recognized in the art as a substrate of α-galactosidase, and the degree of activity is then determined quantitatively. Compounds which allow for particularly convenient detection of α-galactosidase activity are known in the art and are commercially available.

In some embodiments, α-galactosidase activity is determined by assaying hydrolysis of 4-methylumbelliferyl-α-D-galactopyranoside. In other embodiments, α-galactosidase activity is determined by assaying hydrolysis of p-nitrophenyl-α-D-galactopyranoside.

When comparing an activity of a stabilized covalently linked human α-galactosidase protein described herein with an activity of native α-galactosidase, in some specific embodiments the native α-galactosidase preferably comprises α-galactosidase monomers substantially identical (e.g., with respect to amino acid sequence and glycosylation pattern) to the α-galactosidase monomers of the stabilized, covalently-linked recombinant human α-galactosidase protein.

According to some embodiments, the stabilized covalently linked human α-galactosidase of the invention is characterized by a circulating half-life in a physiological system of a human subject which is higher (e.g., at least 20%, at least 50% higher, at least 100% higher, at least 400% higher, at least 900% higher, at least 1500% higher, at least 2000% higher, at least 2500% higher, at least 3000% higher, at least 3500% higher, at least 4000% higher, least 5000% higher, least 7500% higher, least 8000% higher, up to 10,000% higher, up to 20,000% higher, up to 50,000% higher, 100,000% higher, 200,000% higher or greater) than a circulating half-life of non cross-linked α-galactosidase [e.g. Agalsidase alfa (Replagal®, Shire) and agalsidase beta (Fabrazyme®, Genzyme)].

As described herein, when tested in the clinical context, the circulating half-life of the stabilized covalently linked human α-galactosidase of the invention, following IV infusion was remarkably extended. Thus, according to some aspects of the invention the stabilized covalently linked human α-galactosidase of the invention has a circulating half-life ($T_{1/2}$) of at least 5 hours, at least 10 hours, at least 20 hours, at least 50 at least 60 at least 70 at least 80 or at least 90 hours following IV infusion.

In some embodiments, the circulating half-life of the stabilized covalently linked human α-galactosidase of the invention is such that the plasma concentration of the stabilized covalently linked human α-galactosidase of the invention at 14 days post-intravenous administration of 2 mg/Kg body weight is of the same order of magnitude as the maximal plasma concentration of commercially available recombinant human α-galactosidase (agalsidase beta, Fabrazyme®) 2 hours post-infusion with 1 mg/kg body weight).

In some embodiments, the circulating half-life ($T_{1/2}$) of the stabilized covalently linked human α-galactosidase of the invention, when administered intravenously to a subject, is at least 5, 10, 20, 30, 40, at least 50, at least 60, at least 70, at least 80 or at least 90 hours following IV infusion. In some embodiments, the circulating half-life ($T_{1/2}$) following IV infusion of the stabilized covalently linked human α-galactosidase of the invention is in the range of 3-100 hours, in the range of 5-70 hours, in the range of 5-50, 10-45, 15-40, 20-35 40-69 60-80, 60-90 and 25-50 hours. In specific embodiments, the circulating half-life ($T_{1/2}$) of the stabilized covalently linked human α-galactosidase of the invention is between 5 and 10 hours, between 10 and 20 hours, between 20 and 50 hours or between 50 and 80 or between 50 and 90 hours.

In some embodiments, the bioavailability of the stabilized covalently linked human α-galactosidase of the invention can reflect the total available enzyme following administration, expressed as "area under the curve" ($AUC_{0-\infty}$), in units of ug*min/mL or ng*hr/ml. Thus, in some embodiments, bioavailability (area under the curve) of the stabilized covalently linked human α-galactosidase of the invention following intravenous administration of 1.0 mg/Kg stabilized covalently linked human α-galactosidase of the invention to a subject is in the range of 10,000-500,000 ng*hr/ml, 50,000-250,000 ng*hr/ml, at least 10,000 ng*hr/ml, at least 25,000 ng*hr/ml, at least 50,000 ng*hr/ml, at least 75,000 ng*hr/ml, at least 100,000 ng*hr/ml or at least 200,000 ng*hr/ml. In specific embodiments, the bioavailability (area under the curve) of the stabilized covalently linked human α-galactosidase of the invention is 100,000 ng*hr/ml following administration of 1.0 mg/Kg of said recombinant human α-galactosidase.

In other embodiments, the bioavailability (area under the curve) of the stabilized covalently linked human α-galactosidase of the invention following intravenous administration of 2.0 mg/Kg stabilized covalently linked human α-galactosidase of the invention to a subject is in the range of 50,000-800,000 ng*hr/ml, 100,000-600,000 ng*hr/ml, 150,000-500,000 ng*hr/ml, at least 50,000 ng*hr/ml, at least 75,000 ng*hr/ml, at least 100,000 ng*hr/ml, at least 200,000 ng*hr/ml, at least 300,000 ng*hr/ml, at least 400,000 ng*hr/ml or at least 600,000 ng*hr/ml. In specific embodiments, the bioavailability (area under the curve) of the stabilized covalently linked human α-galactosidase of the invention is 400,000 ng*hr/ml following administration of 2.0 mg/Kg of said recombinant human α-galactosidase.

An increased circulating half-life may optionally be associated with a higher in vivo stability (e.g, resistance to metabolism), higher uptake and/or activity at target organs.

Circulating half-lives can be determined by taking samples (e.g., blood samples) from physiological systems (e.g., humans, laboratory animals) at various intervals, and determining a level of α-galactosidase in the sample, using techniques known in the art.

Tissue half-lives can be determined by taking samples (e.g., tissue samples) from physiological systems (e.g., humans, laboratory animals) at various intervals, and determining a level of α-galactosidase in the sample, using techniques known in the art.

Optionally, the half-life is calculated as a terminal half-life (e.g., as described in the Examples section), wherein half-life is the time required for a concentration (e.g., a blood concentration) to decrease by 50% after pseudo-equilibrium of distribution has been reached. The terminal half-life may be calculated from a terminal linear portion of a time vs. log concentration, by linear regression of time vs.

log concentration (see, for example, Toutain & Bousquet-Melou [*J Vet Pharmacol Ther* 2004, 27:427-39]). Thus, the terminal half-life is a measure of the decrease in drug plasma concentration due to drug elimination rate and not of decreases due to other reasons, and is not necessarily the time necessary for the amount of the administered drug to fall by one half.

Determining a level of α-galactosidase (e.g., the stabilized covalently linked human α-galactosidase of the invention or the non-cross linked α-galactosidase) may comprise detecting the physical presence of α-galactosidase (e.g., via an antibody against α-galactosidase) and/or detecting a level of an α-galactosidase activity (e.g., as described herein).

Herein, "human α-galactosidase" refers to a plant recombinant α-galactosidase comprising an amino acid sequence substantially identical (e.g., as described hereinabove) to an amino acid sequence of an α-galactosidase protein which naturally occurs in humans.

Examples of α-GAL suitable for use with the instant invention include without limitation, α-GAL having an amino acid sequence selected from the group consisting of SEQ ID NO: 1, SEQ ID NO: 2, and SEQ ID NO: 3. Optionally, in specific embodiments, the α-GAL has an amino acid sequence selected from the group consisting of SEQ ID NO: 2 and SEQ ID NO: 3. In some embodiments the α-GAL may be any one of SEQ ID NO: 2 or SEQ ID NO: 3. In yet other embodiments, the stabilized covalently linked human α-galactosidase of the invention comprises a population of plant recombinant α-galactosidase comprising a combination of plant recombinant α-galactosidase proteins comprising both α-GAL of SEQ ID NO: 2 and α-GAL of SEQ ID NO: 3.

As used herein, "α-galactosidase" refers to any protein which exhibits an enzymatic activity (e.g., hydrolysis) towards galactose moieties in $Gb_3$ (e.g., α-galactosidase A). Optionally, "α-galactosidase" refers to E.C. 3.2.1.22. As used herein, "acid α-galactosidase" refers to α-galactosidase characterized by an ability to hydrolyse terminal-linked α-galactose moieties from galactose-containing oligosaccharides under acidic pH conditions (e.g., about pH 4.2-5), such as occur in a lysosome.

Optionally, the α-galactosidase protein further comprises at least one mannose-6-phosphate (M6P) moiety. The M6P moiety (or moieties) may be linked to one or more of the α-galactosidase monomers of the α-galactosidase protein (e.g., via a linker).

Techniques and reagents for introducing M6P-containing moieties to a biomolecule (e.g., a polypeptide) are described in WO 2009/024977.

As detailed herein, intravenous administration of the stabilized covalently linked human α-galactosidase of the invention resulted in improvement/stabilization in clinical parameters in human patients, including renal, cardiac and patient (e.g. pain) scores.

Accumulation of Gb3 glycolipid is characteristic of the natural history of Fabry disease, and reduction of its accumulation is a clinical parameter in ERT for Fabry patients. In one embodiment the method of the invention can be used to reduce glycolipid accumulation. Thus, in some embodiments, IV administering the therapeutically effective amount of stabilized covalently linked human α-galactosidase of the invention reduces plasma Gb3 and/or lyso-Gb3 concentrations. In some embodiments, IV administering the therapeutically effective amount of stabilized covalently linked human α-galactosidase of the invention reduces Gb3 (glycolipid) in kidney peritubular capillaries of subjects. In specific embodiments, the reduction is at least 20%, at least 30%, at least 40%, at least 50%, at least 60%, at least 70%, at least 80%, at least 90% reduction or more according to the quantitative BLISS score. In some embodiments, reduction is measured in the BLISS score. Reduction of Gb3 and/or lyso Gb3in response to administration of stabilized covalently linked human α-galactosidase of the invention according to the invention is measured after 1 month, 2 months, 3 months, 5 months, 6 months, one year or more of treatment. In some embodiments, the reduction in Gb3 is at least 50%, when measured at 6 months after commencement of treatment, compared to pre-treatment Gb3.

Fabry patients likewise suffer from pain, and particularly neuropathic pain, and the method and stabilized covalently linked human α-galactosidase of the invention can be used to alleviate Fabry-associated pain in patients. According to some embodiments, administering the therapeutically effective amount of stabilized covalently linked human α-galactosidase of the invention reduces pain in the subjects. Many pain questionnaires are available for assessing pain reduction, a non-limiting list including the McGill Pain Questionnaire, Fabry Pain Questionnaire and Brief Pain Inventory. In some embodiments, the pain reduction is measured according to the Brief Pain Inventory. In some embodiments the pain reduction according to the questionnaire is at least 30%, at least 40%, at least 50% or more. In specific embodiments the reduction in pain is at least 50% reduction. Reduction of pain in response to administration of stabilized covalently linked human α-galactosidase of the invention according to the invention is measured after 1 month, 2 months, 3 months, 5 months, 6 months, one year or more of treatment. In other embodiments, the reduction in pain parameters is measured at 6 months after commencement of treatment, and/or compared to pre-treatment scores.

In some embodiments the reduction in pain is measured 1 week, 2 weeks and 3 weeks within each treatment cycle. In some embodiments the reduction of pain is identified at the second week following administration. In some embodiments the reduction in pain is identified at the third week following administration.

According to other embodiments, administering the therapeutically effective amount of stabilized covalently linked human α-galactosidase of the invention provides improvement in perception of general quality of life in the subjects. Many "quality of life" questionnaires are available for assessing treatment outcome, a non-limiting list including the McGill Quality of Life Questionnaire, Quality of Life Scale (QOLS), WHO Quality of Life (WHOQOL) and the EQ-5D-5L questionnaire. In some embodiments, quality of life is measured according to the EQ-5D-5L questionnaire, which comprises 5 dimensions of health: mobility, ability for self-care, ability to undertake usual activities, pain and discomfort, and anxiety and depression. There are 5 option levels under each domain. In some embodiments the improvement according to the questionnaire is at least 30%, at least 40%, at least 50% or more. In specific embodiments the improvement in quality of life is at least 50% improvement. Improvement in quality of life in response to administration of stabilized covalently linked human α-galactosidase of the invention according to the invention is measured after 1 month, 2 months, 3 months, 5 months, 6 months, one year or more of treatment. In other embodiments, the improvement in quality of life is measured at 6 months after commencement of treatment, and/or compared to pre-treatment scores.

Kidney impairment is another common clinical complication of Fabry disease, mainly caused by accumulation of glycolipid in kidney tubules, and characterized by progressive deterioration over the course of the disease leading to end-stage renal disease. The method and stabilized covalently linked human α-galactosidase of the invention can be used to slow the progress of the nephropathy and approach stabilization of kidney function, or maintain a steady level of kidney function in a patient. Thus, according to some embodiments, administering the therapeutically effective amount of stabilized covalently linked human α-galactosidase of the invention using the methods of the present invention attenuates Fabry nephropathy in the subjects.

Thus, according to other embodiments, administering the therapeutically effective amount of stabilized covalently linked human α-galactosidase of the invention using the methods of the present invention maintains a steady level of kidney nephropatic function in the subjects.

Methods for assessing kidney function in Fabry patients include, but are not limited to laboratory markers (proteinuria, microalbuminuria, chronic kidney disease (CKD) assessment, etc), macroscopic hematuria, biopsy, electron microscopy of biopsy, impaired kidney function, and renal ultrasonography and MRI abnormalities. In some embodiments, kidney function (and impaired kidney function, or nephropathy) is measured according glomerular filtration rate and/or proteinuria score. Glomerular filtration rate (GFR) is the volume of fluid filtered from the renal (kidney) glomerular capillaries into the Bowman's capsule per unit time. There are several different techniques used to calculate or estimate the glomerular filtration rate (GFR or eGFR). In clinical practice, creatinine clearance or estimates of creatinine clearance based on the serum creatinine level are used to estimate GFR. Most commonly used methods for Estimated GFR (eGFR) using Modification of Diet in Renal Disease (MDRD) formula, (using four variables: serum creatinine, age, ethnicity, and gender), and CKD-EPI formula (Chronic Kidney Disease Epidemiology Collaboration), developed in an effort to create a formula more accurate than the MDRD formula.

In some embodiments there is an attenuation of deterioration in kidney function. Attenuation of deterioration of kidney function in response to IV administration of stabilized covalently linked human α-galactosidase of the invention according to some aspects of the invention is measured after 3 months, 6 months, 12 months, 24 months, or more of treatment. In other embodiments, the attenuation of Fabry-related kidney deterioration is measured at 6 months after commencement of treatment, and/or compared to pre-treatment scores. In specific embodiments the kidney function is maintained at a steady level, the same as or similar to when treatment is initiated, as measured using estimated glomerular filtration rate and/or proteinuria score following 6 months, 12 months, 24 months, or more of treatment.

In some embodiments administering the therapeutically effective amount of stabilized covalently linked human α-galactosidase of the invention improves at least one gastrointestinal parameter in the subjects. In some embodiments, the gastrointestinal parameter includes, but is not limited to abdominal pain and or frequency of abdominal pain. In some embodiments there is an attenuation of the frequency of GI related signs and symptoms. In other embodiments, the reduction in gastrointestinal parameters is measured at 6 months after commencement of treatment, and/or compared to pre-treatment status.

In specific embodiments the Fabry-associated gastrointestinal parameters remain at a similar steady level, as measured following, 2 months, 4 months, 6 months, 12 months or more of treatment.

In some embodiments administering the therapeutically effective amount of stabilized covalently linked human α-galactosidase of the invention improves/stabilizes at least one cardiac parameter in the subjects. Cardiac parameters include, but are not limited to ECG components, cardiac function (e.g. ejection fraction), arrhythmias, valvular malfunction and cardiac hypertrophy. In other embodiments, cardiac parameters are LVM and LVMI, measured by MRI. Improvement/stabilization in cardiac parameters in response to IV administration of stabilized covalently linked human α-galactosidase of the invention according to some aspects of the invention is measured after 6 months, 12 months, 24 months, or more of treatment. In other embodiments, the reduction in LVM or LVMI, measured by MRI is measured at 6 months after commencement of treatment, and/or compared to pre-treatment values.

In specific embodiments the cardiac parameters remain at a steady level, as measured at treatment initiation, following 6 months, 12 months, 24 months, or more of treatment.

In other embodiments, the state of a patient's Fabry disease can be assessed by the Mainz Severity Score Index (MSSI), which is a tool for quantifying the Fabry disease burden, the combined signs and symptoms of the disease. The MSSI can thus be used to assess disease state in patients treated with the alpha galactosidase protein and methods of the invention. Thus, according to some embodiments, administering the therapeutically effective amount of stabilized covalently linked human α-galactosidase of the invention maintains a steady or improved MSSI score in subjects. MSSI score in response to administration of stabilized covalently linked human α-galactosidase of the invention according to some aspects of the invention can be measured after 6 month, 12 months, 24 months, or more of treatment. In other embodiments, the reduction in MSSI is measured at 6 months after commencement of treatment, and/or compared to pre-treatment scores.

In other specific embodiments the state of a patient's Fabry disease as measured with MSSI remains at a steady level, as measured at treatment initiation, following 6 month, 12 months, 24 months or more of treatment.

According to another aspect of embodiments of the invention, there is provided a pharmaceutical composition that comprises a stabilized covalently linked human α-galactosidase of the invention as described herein and a pharmaceutically acceptable carrier. In some embodiments, the stabilized covalently linked human α-galactosidase of the invention comprises a stabilized covalently-linked plant recombinant human alpha galactosidase protein.

As used herein a "pharmaceutical composition" refers to a preparation of one or more of the stabilized covalently linked human α-galactosidase protein of the invention described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The pharmaceutical composition optionally comprises an additional ingredient which further stabilizes the α-galactosidase of the stabilized covalently linked human α-galactosidase of the invention. Optionally, the additional ingredient is galactose.

Alternatively, a galactose derivative (e.g., a galactose-containing glycoside) may be used instead of galactose. Optionally, a non-reducing galactose derivative is used.

Techniques for formulation and administration of drugs may be found in "Remington's Pharmaceutical Sciences" Mack Publishing Co., Easton, PA, latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of stabilized covalently linked human α-galactosidase of the invention into preparations which can be used pharmaceutically. Proper formulation is dependent upon the route of administration chosen.

For injection or infusion, the stabilized covalently linked human α-galactosidase of the invention may be formulated in aqueous solutions, preferably in physiologically compatible buffers such as Hank's solution, Ringer's solution, or physiological saline buffer with or without organic solvents such as propylene glycol, polyethylene glycol.

The stabilized covalently linked human α-galactosidase of the invention can be formulated as part of an aqueous fluid suspension or solution for intravenous (IV) administration.

The stabilized covalently linked human α-galactosidase of the invention described herein may be formulated for parenteral administration, e.g., by bolus injection or continuous infusion. Formulations for injection or infusion may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the stabilized covalently linked human α-galactosidase of the invention in water-soluble form. Additionally, suspensions of the stabilized covalently linked human α-galactosidase of the invention may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the stabilized covalently linked human α-galactosidase of the invention to allow for the preparation of highly concentrated solutions.

The formulations of the present invention can be used with the methods described herein or with other methods for treating Fabry disease. Formulations of the stabilized covalently linked human α-galactosidase of the invention may be further diluted before administration to a subject. In some embodiments, the formulations will be diluted with saline and held in IV bags or syringes before administration to a subject.

In typical embodiments, the stabilized covalently linked human α-galactosidase of the invention is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed, for example, with an infusion bottle containing sterile pharmaceutical grade water or saline. Where the pharmaceutical is administered by injection, an ampoule of sterile water for injection or saline can be, for example, provided so that the ingredients can be mixed prior to administration.

Alternatively, stabilized covalently linked human α-galactosidase of the invention may be in powder form for constitution with a suitable vehicle, e.g., sterile, pyrogen-free water, before use.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in the context of the present invention include compositions wherein the active ingredients are contained in an amount effective to achieve the intended purpose. More specifically, a therapeutically effective amount means an amount of stabilized covalently linked human α-galactosidase of the invention effective to prevent, alleviate or ameliorate symptoms of disease, improve quality of life or prolong the survival of the subject being treated.

For any stabilized covalently linked human α-galactosidase used in the methods of the invention, the therapeutically effective amount or dose can be estimated initially from activity assays in animals. For example, a dose can be formulated in animal models to achieve a circulating concentration range that includes the $IC_{50}$ as determined by activity assays (e.g., the concentration of the test stabilized covalently linked human α-galactosidase protein, which achieves a half-maximal increase in a biological activity of the stabilized covalently linked human α-galactosidase protein). Such information can be used to more accurately determine useful doses in humans.

As is demonstrated in the Examples section that follows, a therapeutically effective amount for the stabilized covalently linked human α-galactosidase of embodiments of the present invention may range between 0.1 mg/kg body weight and about 5.0 mg/kg body weight. In some embodiments, a therapeutically effective amount for the stabilized covalently linked human α-galactosidase of the invention may be any one of 0.1, 0.2, 0.5, 0.75, 1.0, 1.25, 1.50, 1.75, 2.0, 2.25, 2.5, 2.75, 3.0, 3.25, 3.50, 3.75, 4.0, 4.25, 4.50, 4.75 or 5.00 mg/Kg body weight. In specific embodiments, a therapeutically effective amount of the stabilized covalently linked human α-galactosidase of the invention is 1.0 mg/kg body weight. In other specific embodiments, a therapeutically effective amount for the stabilized covalently linked human α-galactosidase of the invention is 2.0 mg/kg body weight. In yet other specific embodiments, a therapeutically effective amount for the stabilized covalently linked human α-galactosidase of the invention is 5.0 mg/kg body weight. In general, toxicity and therapeutic efficacy of the stabilized covalently linked human α-galactosidase of the invention described herein can be determined by standard pharmaceutical procedures in experimental animals, e.g., by determining the $EC_{50}$, the $IC_{50}$ and the $LD_{50}$ (lethal dose causing death in 50% of the tested animals) for a subject protein structure. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects. In some embodiments, the stabilized covalently linked human α-galactosidase of the invention is administered by intravenous infusion at a rate of 20-200 ml/hr. In specific embodiments, for example, the stabilized covalently linked human α-galactosidase of the invention is delivered in total volume of 150 ml and for dosages of less than 2.0 mg/ml, infusion rates can be 37.5 or 75 ml/hr for patients weighing less than 75 Kg, and 25.2 ml/hr for patients weighing more than 75 Kg. In yet other embodiments, the stabilized covalently linked human α-galactosidase of the invention is delivered in total volume of 350 ml, and for dosages of 2.0 mg/kg body weight, infusion rates can be 58.2 ml/hr for patients weighing less than 90 Kg, with infusion rates individually determined for patients weighing more than 90 Kg. In still other embodiments, the stabilized covalently linked human α-galactosidase of the invention is delivered in 150 ml volume for example, in patients weighing up to 70 Kg, in a total volume of 250 ml, for example, for patients weighing between 70 and 100 Kg, and in a total volume of 500 ml per infusion, for example, for patients weighing over 100 Kg, at rates of 0.83 mL/min (50 ml/hr) for 150 ml infusion, 1.38 mL/min (82.2 ml/hr) for 250 ml infusion and 2.78 ml/min (167 ml/hr) for 500 ml infusions.

Infusion times may be altered, after observation of tolerance of the patients for the treatments. In some embodiments, the infusion time can be reduced gradually to 1.5 hours, based on administering physician's evaluation.

In some embodiments, infusion time can be up to 8 hours from commencement until completion of the desired dosage of the stabilized covalently linked human α-galactosidase of the invention. In some embodiments, infusion time is 1, 2, 3, 4.5, 5, 6, 7 or 8 hours. In some cases infusion time can exceed 8 hours, in accordance with the individual circumstances and needs of individual subjects.

In some embodiments, (e.g. where the dosage of the stabilized covalently linked human α-galactosidase of the invention is 2.0 mg/Kg), intravenous infusions may be administered along with a premedication protocol including but not limited to an H1 blocker (diphenhydramine, hydroxyzine, cetrizine, loratadine, desloratadine), and an H2 blocker (ranitidine, cimetidine, famotidine) at standard doses 12 hours and/or 2 hours before the start of the infusion.

Surprisingly, when administered to Fabry patients, the stabilized covalently linked human α-galactosidase of the invention exhibited superior, extended bioavailability (see Examples III-V, hereinbelow) compared to conventional available alpha-galactosidase preparations used in Fabry ERT. Thus, the stabilized covalently linked human α-galactosidase of the invention will have prolonged bioavailability not only during the demonstrated 2 week period following administration, but up until the $3^{rd}$ and $4^{th}$ weeks following intravenous administration.

Thus, in specific embodiments, the stabilized covalently linked human α-galactosidase of the invention of the present invention is administered intravenously, as an infusion, at dosage intervals of greater than two weeks (14 days ±3 days). In some embodiments, the stabilized covalently linked human α-galactosidase of the invention of the present invention is administered intravenously, as an infusion, at dosage intervals of greater than two weeks (14 days ±3 days) and up to four weeks (28 days, ±3 days). In some embodiments the interval may be any one of 15 days, 16 days, 17 days, 18 days, 19 days, 20 days, 21 days (3 weeks), 22 days, 23 days, 24 days, 25 days, 26 days, 27 days or 28 days (4 weeks), 29 days, 30 days, 31 days (a month), 32 days, 33 days, 34 days, 35 days (5 weeks), 36 days, 37 days, 38 days, 39 days, 41 days, 42 days (6 weeks), 43 days, 44 days, 45 days, 46 days, 47 days, 48 days, 49 days (7 weeks), 50 days, 51 days, 52 days, 53 days, 54 days, 55 days or 56 days(8 weeks). In some embodiments, the stabilized covalently linked human α-galactosidase of the invention of the present invention is administered intravenously, as an infusion, at dosage intervals of greater than two weeks (14 days ±3 days) and up to eight weeks (56 days, ±3 days). In some embodiments, the stabilized covalently linked human α-galactosidase of the invention of the present invention is administered intravenously, as an infusion, at dosage intervals of 17 days to 8 weeks, 17 days to 6 weeks, 17 days to 5 weeks, 3 weeks to 6 weeks, 3 weeks to 5 weeks, 3 weeks to 4 weeks, 4 weeks to 6 weeks or 4 weeks to 5 weeks. In specific embodiments, the stabilized covalently linked human α-galactosidase of the invention, is administered intravenously at intervals in the range of once every 6 weeks ±3 days. In other embodiments, the interval is once every 6 weeks. In specific embodiments, the stabilized covalently linked human α-galactosidase of the invention, is administered intravenously at intervals in the range of once every 5 weeks ±3 days. In other embodiments, the interval is once every 5 weeks. In specific embodiments, the stabilized covalently linked human α-galactosidase of the invention, is administered intravenously at intervals in the range of once every 4 weeks ±3 days (e.g. monthly). In other embodiments, the interval is once every 4 weeks. In one embodiment, the stabilized covalently linked human α-galactosidase of the invention protein is administered at intervals of three weeks ±3 days between administrations.

In another embodiment, the stabilized covalently linked human α-galactosidase of the invention is administered at intervals of three weeks between administrations. In yet other embodiments, the stabilized covalently linked human α-galactosidase of the invention is administered at a dosage of 1.0 mg/Kg body weight, at intervals of three weeks between administrations. In still other embodiments, the stabilized covalently linked human α-galactosidase of the invention is administered at a dosage of 2.0 mg/Kg body weight, at intervals of three weeks between administrations. In yet other embodiments, the stabilized covalently linked human α-galactosidase of the invention is administered at a dosage of 1.0 mg/Kg body weight, at intervals of 4 weeks between administrations. In still other embodiments, the stabilized covalently linked human α-galactosidase of the invention is administered at a dosage of 2.0 mg/Kg body weight, at intervals of 4 weeks between administrations.

In order to facilitate administration of the stabilized covalently linked human α-galactosidase of the invention according to the method (e.g. regimen) of the present invention, the stabilized covalently linked human α-galactosidase of the invention can be provided in a unit dosage form formulated for intravenous administration, or as a pharmaceutical composition formulated for intravenous administration (infusion).

Thus, according to an aspect of the invention there is provided a unit dosage form comprising 2.0-500 mg stabilized covalently linked human α-galactosidase of the invention formulated for administration to a human subject. It will be appreciated that this range is aimed at a minimal dose administered at intervals greater than 2 weeks and up to 4 weeks to maximal dose administered at intervals greater than 2 weeks and up to 4 weeks in patients weighing from 10-250 Kg.

According to an embodiment the unit dosage form comprises 2.0-500 mg stabilized covalently linked human α-galactosidase of the invention formulated for administration to a human subject.

According to an embodiment the unit dosage form comprises 5.0-470 mg stabilized covalently linked human α-galactosidase of the invention formulated for administration to a human subject.

According to an embodiment the unit dosage form comprises 10.0-450 mg stabilized covalently linked human α-galactosidase of the invention formulated for administration to a human subject.

According to an embodiment the unit dosage form comprises 17.0-425 mg stabilized covalently linked human α-galactosidase of the invention formulated for administration to a human subject.

According to an embodiment the unit dosage form comprises 21.0-400 mg stabilized covalently linked human α-galactosidase of the invention formulated for administration to a human subject.

According to an embodiment the unit dosage form comprises 35.0-370 mg stabilized covalently linked human α-galactosidase of the invention formulated for administration to a human subject.

According to an embodiment the unit dosage form comprises 55.0-340 mg stabilized covalently linked human α-galactosidase of the invention formulated for administration to a human subject.

According to an embodiment the unit dosage form comprises 75.0-300 mg stabilized covalently linked human α-galactosidase of the invention formulated for administration to a human subject.

According to an embodiment the unit dosage form comprises 90.0-270 mg stabilized covalently linked human α-galactosidase of the invention formulated for administration to a human subject.

According to an embodiment the unit dosage form comprises 100.0-225 mg stabilized covalently linked human α-galactosidase of the invention formulated for administration to a human subject.

According to an embodiment the unit dosage form comprises 100.0-200 mg stabilized covalently linked human α-galactosidase of the invention formulated for administration to a human subject.

According to an embodiment the unit dosage form comprises 110.0-190 mg stabilized covalently linked human α-galactosidase of the invention formulated for administration to a human subject.

According to an embodiment the unit dosage form comprises 120.0-175 mg stabilized covalently linked human α-galactosidase of the invention formulated for administration to a human subject.

According to an embodiment the unit dosage form comprises 130.0-150 mg stabilized covalently linked human α-galactosidase of the invention formulated for administration to a human subject.

According to an embodiment the unit dosage form comprises 10.0 mg stabilized covalently linked human α-galactosidase of the invention formulated for administration to a human subject.

According to an embodiment the unit dosage form comprises 30.0 mg stabilized covalently linked human α-galactosidase of the invention formulated for administration to a human subject.

According to an embodiment the unit dosage form comprises 50.0 mg stabilized covalently linked human α-galactosidase of the invention formulated for administration to a human subject.

According to an embodiment the unit dosage form comprises 75.0 mg stabilized covalently linked human α-galactosidase of the invention formulated for administration to a human subject.

According to an embodiment the unit dosage form comprises 100.0 mg stabilized covalently linked human α-galactosidase of the invention formulated for administration to a human subject.

According to an embodiment the unit dosage form comprises 125.0 mg stabilized covalently linked human α-galactosidase of the invention formulated for administration to a human subject.

According to an embodiment the unit dosage form comprises 150.0 mg stabilized cross-linked plant recombinant human alpha galactosidase protein formulated for administration to a human subject.

According to an embodiment the unit dosage form comprises 175.0 mg stabilized covalently linked human α-galactosidase of the invention formulated for administration to a human subject.

According to an embodiment the unit dosage form comprises 200.0 mg stabilized covalently linked human α-galactosidase of the invention formulated for administration to a human subject.

According to an embodiment the unit dosage form comprises 250.0 mg stabilized covalently linked human α-galactosidase of the invention formulated for administration to a human subject.

According to an embodiment the unit dosage form comprises 300.0 mg stabilized covalently linked human α-galactosidase of the invention formulated for administration to a human subject.

According to an embodiment the unit dosage form comprises 350.0 mg stabilized covalently linked human α-galactosidase of the invention formulated for administration to a human subject.

According to an embodiment the unit dosage form comprises 400.0 mg stabilized covalently linked human α-galactosidase of the invention formulated for administration to a human subject.

According to an embodiment the unit dosage form comprises 430.0 mg stabilized covalently linked human α-galactosidase of the invention formulated for administration to a human subject.

According to an embodiment the unit dosage form comprises 480.0 mg stabilized covalently linked human α-galactosidase of the invention formulated for administration to a human subject.

According to an embodiment the unit dosage form comprises 500.0 mg stabilized covalently linked human α-galactosidase of the invention formulated for administration to a human subject.

The method of treating Fabry disease in a human subject, according to the present invention, can be provided as a stand-alone treatment for Fabry disease, or can be combined with additional treatment options, conventional or unconventional treatments. Fabry patients suitable for treatment with the method or stabilized covalently linked human α-galactosidase of the invention can also be receiving, before, during or after treatment with the method or protein of the invention, for example, treatment with non-ERT therapeutics such as, but not limited to Migalastat hydrochloride (Chaperone Amicus Therapeutics), Ibiglustat (INN) (a glucosyl ceramide synthase (GCS) inhibitor) (Genzyme Corp), Lucerastat (INN)—a piperadine derivative (Actelion Ltd), NP-003—(a Glycoprotein-1 (MDR-1 or ABCB1) inhibitor) (Neuraltus Pharmaceuticals, Inc), SBLSD-4— (Gene therapy (In vivo gene editing)—Sangamo BioSciences, Inc.), Genz-78132 (a glucosyl ceramide synthase (GCS) inhibitor) (Genzyme Corporation), Miglustat—(a glucosyl ceramide synthase (GCS) inhibitor GlaxoSmithKline Plc and Actelion Ltd).

Fabry patients suitable for treatment with the method or stabilized covalently linked human α-galactosidase of the invention can also be receiving, before or after treatment with the method or stabilized covalently linked human α-galactosidase of the invention treatment with ERTs therapeutics and regimens such as, but not limited to Fabrazyme® and Replagal® or pegunigalsidase alfa in the conventional regimen.

Patient populations suitable for treatment with the method or protein of the invention include Fabry patients of all ages both males and females, and Fabry patients with or without severe symptoms, slow progressing patients, early diagnosed as well as patients with established Fabry disease, young patients and patients with steady Fabry disease.

As used herein, "steady" Fabry patients refers to Fabry patients who maintain the level of at least one of the Fabry disease parameters over a pre-determined time period and/or maintain a similar rate of deterioration in that parameter (e.g. cardiac, renal [such as eGFR decline], pain, gastrointestinal and biomarkers [such as, plasma or urine Gb3 and lyso-Gb3] and the like). In some embodiments, steady Fabry patients can include patients from populations comprising newly diagnosed Fabry patients with mild to moderate severity of symptoms, naïve patients and patients previously treated for Fabry disease. In some embodiments, the steady Fabry patients include patients who were steady before initiation of treatment with the methods and/or compositions of the invention.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA/EMA (the U.S. Food and Drug Administration European Medicinal Agency) approved kit, which may contain one or more unit dosage forms containing the active ingredient. The pack may, for example, comprise metal or plastic foil, such as, but not limited to a blister pack or a pressurized container. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert or by the EMA or any other regulatory body. Compositions comprising a protein structure of embodiments of the invention formulated in a compatible pharmaceutical carrier may also be prepared, placed in an appropriate container, and labeled for treatment of an indicated condition or diagnosis, as is detailed herein.

Thus, according to an embodiment of the present invention, depending on the selected stabilized covalently linked human α-galactosidase of the invention, the pharmaceutical composition described herein is packaged in a packaging material and identified in print, in or on the packaging material, for use in the treatment of a condition in which the activity of the cross-linked protein structure is beneficial, as described hereinabove.

In some embodiments the packaging material, pack or dispenser, kit or container may comprise or be accompanied by instructions for administration of the stabilized covalently linked human α-galactosidase or compositions comprising the same to the subject in need thereof. In some embodiments, instructions for administration can be included within a label affixed to the containers and/or vials containing the stabilized covalently linked human α-galactosidase or compositions comprising the same of the invention.

Instructions for use and administration may include, inter alia, specific indications (e.g. Fabry disease), directions for preparation of the stabilized covalently linked human α-galactosidase or compositions of the invention the same for administration, details for administering the stabilized covalently linked human α-galactosidase or compositions of the invention and post-administration protocol, and details regarding the dosage and regimen for treatment with the stabilized covalently linked human α-galactosidase or compositions comprising the same of the invention. In specific embodiments, the instructions can include directions for intravenous administration of the stabilized covalently linked human α-galactosidase of the invention of the present invention, as an infusion, at dosage intervals of greater than two weeks (14 days ±3 days), once every three weeks, or once every 4 weeks ±3 days (e.g. monthly). In other embodiments, the instructions include directions for administration at a dosage interval of once every 4 weeks. In a further embodiment, the instructions include directions for administration of the stabilized covalently linked human α-galactosidase of the invention at intervals of three weeks ±3 days between administrations.

As used herein the term "about" refers to ±10%

The terms "comprises", "comprising", "includes", "including", "having" and their conjugates mean "including but not limited to".

The term "consisting of" means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example I

Clinical Trial Protocol: A Phase 1/2, Open Label, Dose Ranging Study to Evaluate the Safety, Tolerability, Pharmacokinetics and Exploratory Efficacy Parameters of Pegunigalsidase Alfa, Administered by Intravenous Infusion Every 2 Weeks to Adult Fabry Patients This study assesses the safety, tolerability, pharmacokinetics and exploratory efficacy of plant recombinant human α-galactosidase cross-linked with bis-NHS-PEG45 (prh-alpha-GAL-I-CL45) (pegunigalsidase alfa) in the target population. Subjects were required to have a definitive diagnosis of Fabry disease based on alpha-GAL-A activity (males) or genetic testing (females) with manifestations of the disease, and not to have been treated with ERT in the last 6 months. The parameters chosen as endpoints were the parameters most relevant to the disease and allow a significant and relevant evaluation of safety pharmacokinetics and efficacy endpoints. The study of three dose levels provided important information on 3 dose levels regarding safety, tolerability and clinical outcome.

Selection of Study Population
Inclusion Criteria:
1. Symptomatic adult Fabry patients (≥18 yrs, males and females)
2. Males: plasma and/or leucocyte alpha galactosidase activity (by activity assay) less than lower limit of normal (LLN in plasma=3.2 nmol/hr/ml, LLN in leucocytes=32 nmol/hr/mg/protein)
3. Females: historical genetic test results consistent with Fabry mutations
4. Globotriaosylceramide (Gb3) concentration in urine >1.5 times upper normal limit
5. Patients who have never received enzyme replacement therapy (ERT) in the past, or patients who have not received ERT in the past 6 months and have a negative anti pegunigalsidase alfa antibody test
6. eGFR ≥60 mL/min/1.73 m$^2$
7. Signing of informed consent
8. Female patients and male patients whose co-partners are of child-bearing age potential agreed to use a medically acceptable method of contraception, not including the rhythm method Exclusion Criteria
The presence of any of the following excluded a subject from enrollment:
1. Participation in any trial of an investigational drug within 30 days prior to study screening
2. Treatment with any of Fabrazyme® (agalsidase-beta), Replagal® (agalsidase-alfa), or any other investigational drug for treating Fabry disease
3. Chronic kidney disease stages 3-5 (CKD 3-5)
4. History of dialysis or renal transplantation 5. Angiotensin converting enzyme (ACE) inhibitor or angiotensin receptor blocker (ARB) therapy initiated or dose changed in the 4 weeks prior to screening 6. Severe myocardial fibrosis by MRI (≥2 late-enhancement [LE] positive left ventricular segments) (Weidemann et al. 2009)

7. History of clinical stroke

8. Pregnant or nursing

9. Presence of HIV and/or HBsAg and/or Hepatitis C infections

10. Known allergies to ERT

11. Known allergy to Gadolinium based contrast agents

12. Presence of any medical, emotional, behavioral or psychological condition that, in the judgment of the Investigator and/or Medical Director, would have interfered with the patient's compliance with the requirements of the study.

Drug Administration

All infusions were given during hospitalization, with observation period post-infusion with option for outpatient monitoring where required.

Three Treatment Groups made up the subject population. Treatment Group I: 0.2 mg/kg every 2 weeks. Treatment Group II: 1 mg/kg every 2 weeks. Treatment Group III: 2 mg/kg every 2 weeks.

Subjects (4-8 patients per group) received intravenous infusions every 2 weeks 14 days).

Pharmacokinetics (PK) Parameters

The following PK parameters are derived from the plasma concentration versus time profiles to determine the profile of the study drug: $C_{max}$, $t_{1/2}$, $T_{max}$, $AUC_{0-t}$, and $AUC_{0-\infty}$. Samples were taken at Day 1 of treatment (first infusion), at the 3M visit infusion, at the 6M visit infusion and at the 12M visit infusion. Blood for PK was withdrawn at the following time points: pre-infusion (baseline); 1 hour after the beginning of the infusion; at the end of the infusion; 1, 4, 8, 24, 48±3, 72±3, 96±3 hours and 2 weeks ±3 days post-infusion (last blood sample was drawn just before the next infusion of the patient.

Efficacy Variable(s)

Efficacy parameters evaluated for analysis of endpoints as follows:
  Gb3 concentrations in plasma and urine sediment at baseline and at every infusion during the study
  Globotriaosylsphingosine (Lyso-Gb3) concentration in plasma at baseline and at every infusion during the study
  Assessment of gastrointestinal symptoms at baseline and at last infusion
  Kidney functions (eGFR and proteinuria) at baseline and at last infusion
  Short Form Brief Pain Inventory (BPI) at baseline and at last infusion.

The following additional procedures were optionally performed at baseline.
  Kidney biopsy for Gb3 concentration
  Skin punch biopsy for Gb3 concentration
  MRI of the heart and brain
  Mainz Severity Score Index (MSSI)
  Cardiac function assessment (echocardiography and stress test)

Safety Variables

Safety was assessed by the frequency, severity, and duration of treatment-emergent AEs (adverse events), including clinically significant laboratory abnormalities, ECG changes from baseline, physical examination findings and assessment of the injection site after administration of the study drug.

Anti-(pegunigalsidase alfa) antibodies were assessed before dosing at: baseline, every month, at last infusion, and 1 and 3 months after last infusion.

Clinical Laboratory Assessment

The following clinical parameters were also assessed over the course of administration of plant recombinant human α-galactosidase cross-linked with bis-NHS-PEG$_{45}$ (prh-alpha-GAL-I-CL45, pegunigalsidase alfa):

Hematology: complete blood count; total white blood cell count with differential (neutrophils, lymphocytes, monocytes, eosinophils and basophils), total red blood cells (hemoglobin, hematocrit, mean corpuscular volume, mean corpuscular hemoglobin and mean corpuscular hemoglobin concentration), and platelets.

Coagulation profile: prothrombin time (PT) and partial thromboplastin time (PTT)

Biochemistry: sodium, potassium, glucose, blood urea nitrogen, creatinine, calcium, phosphate (inorganic), uric acid, total protein, albumin, bilirubin (total), alkaline phosphatase, aspartate transaminase, alanine transaminase, gamma-glutamyl transferase, lactate dehydrogenase, and creatine phosphokinase Urinalysis: dipstick for presence of blood, glucose, ketones, and protein Anti-Pegunigalsidase Alfa Antibodies Anti-pegunigalsidase alfa, including neutralizing antibodies in subjects having a positive IgG antibody response were assessed.

Adverse Events (AE) and Serious Adverse Events (SAE)

An adverse event (AE) is defined as any untoward medical occurrence in a subject participating in a clinical trial, including any unfavorable and unintended sign, symptom or disease temporally associated with the use of pegunigalsidase alfa, whether or not considered related to the study medication. AEs were collected from the start of treatment until 90 days following the final visit dose. AE also includes accidental injuries, reasons for any change in medication (drug and/or dose) other than planned titration, reasons for admission to a hospital, or reasons for surgical procedures (unless for minor elective surgery for a pre-existing condition).

Example II

Pegunigalsidase Alfa is Safe and Effective in Reducing Fabry Disease Symptoms

Patients were monitored for safety (Adverse Effects) and improvement in clinical parameters following IV treatment with 0.2 mg/Kg, 1.0 mg/Kg and 2.0 mg/Kg of pegunigalsidase alfa. Safety data indicated that pegunigalsidase alfa is well tolerated, with a low incidence of adverse effects (AE) among the 18 patients. Pegunigalsidase alfa was also effective in reducing plasma and kidney peritubular capillary globotriacosylceramide (Gb3).

A significant reduction in plasma Gb3 and lysoGb3 was also observed in male patients when monitored after 6 months of treatment with pegunigalsidase alfa. Kidney function (eGFR and Urine protein/creatinine) remained stable in all patients throughout 12 months of treatment with pegunigalsidase alfa. Thus, treatment with pegunigalsidase alfa, administered bi-weekly, is clearly both safe and effective for Fabry patients.

Example III

Pharmacokinetic Profile of Pegunigalsidase Alfa

Cross-Linking Enhances Bio-Availability of Pegunigalsidase Alfa

Pharmacokinetic parameters were monitored in patients receiving 0.2 mg/Kg, 1.0 mg/Kg and 2.0 mg/Kg pegunigalsidase alfa, on Day 1 of treatment (first infusion), at the 3M visit IV infusion, at the 6M visit IV infusion and at the 12M visit IV infusion, based on the pegunigalsidase alfa plasma levels. Blood for PK was withdrawn immediately prior to administration and throughout the 14 days between treatments.

Figure 2:
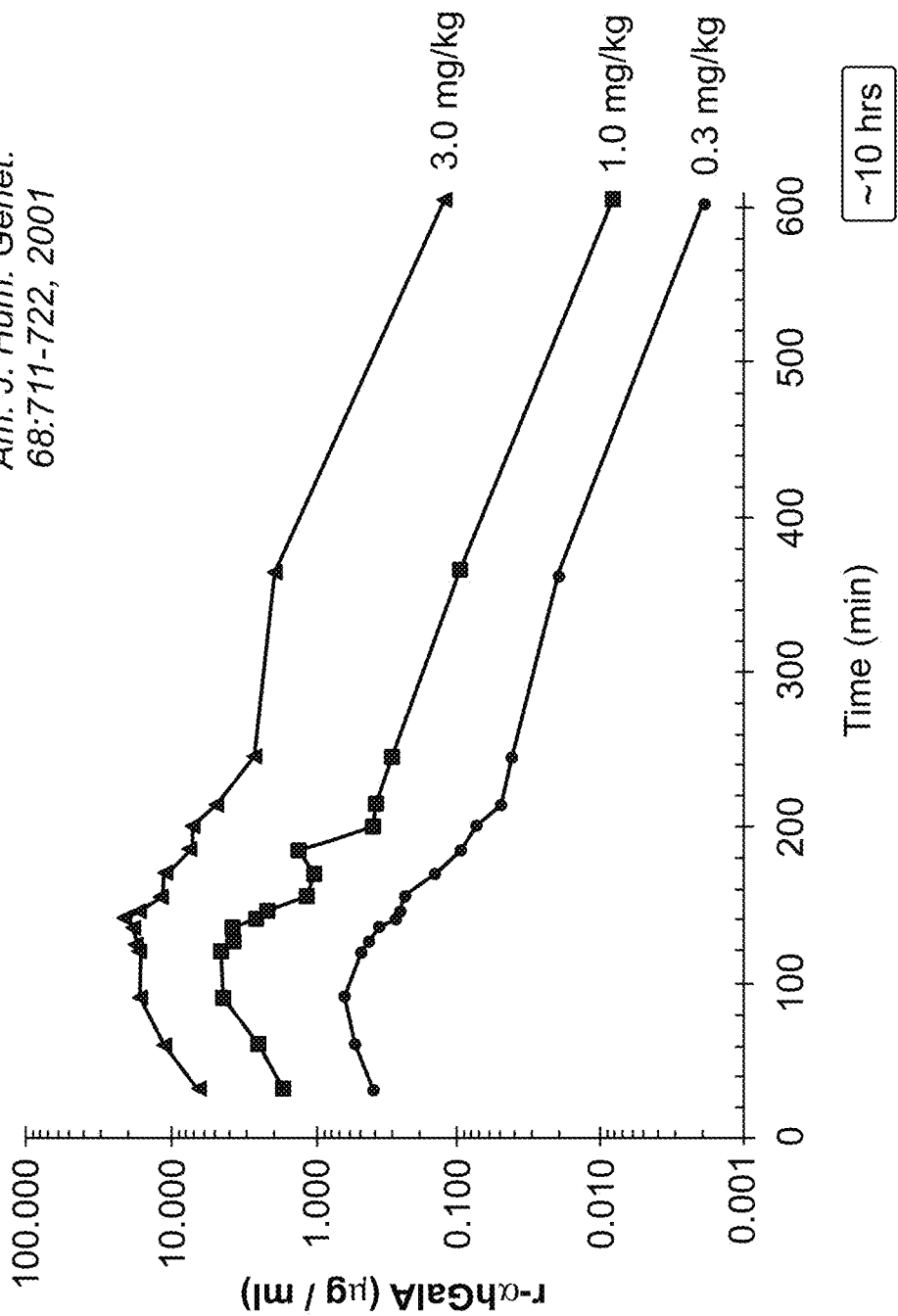
FIG. 2 is a graph from publically available PK data showing the pharmacokinetic profile of commercially available Algasidase beta (r-alphahGalA, mammalian cell recombinant human α-GAL A, Fabrazyme™, Genzyme Corp, Cambridge MA), over approximately 10 hours (600 min) following initiation of administration (infusion), on a logarithmic scale. The data is from American Journal of Human Genetic s, 68, 711-722, 2001. Note the short-term (approx. 10 hours) bioavailability of all concentrations of Algalsidase beta, compared with that of pegunigalsidase alfa for similar dosage (measureable in days) (see FIG. 1)

Significant plasma concentration of the enzyme (measured by immunoassay using anti-pegunigalsidase alfa antibodies) was clearly detectable over the entire 14 days following administration, for all dosages (see examples in FIG. 1), in a dose-dependent manner. In all dosages, the plasma concentration peaked soon after administration, and exhibited a slow, steady decline throughout the next 14 days. FIG. 2 shows a pharmacokinetic profile for plasma concentration of clinically approved commercial Agalsidase beta (r-alphahGalA, mammalian cell recombinant human α-GAL A, Fabrazyme™, Genzyme Corp, Cambridge MA), following administration. In stark contrast to the pharmacokinetic profile of pegunigalsidase alfa, Agalsidase beta, as is evident from the graph, is barely detectable in patients' plasma by 10 hours following administration. Thus, pegunigalsidase alfa appears to have a much enhanced bioavailability, extending further than the 14 days illustrated herein, and clearly superior to that of the clinically approved Fabrazyme™.

Figure 3C:
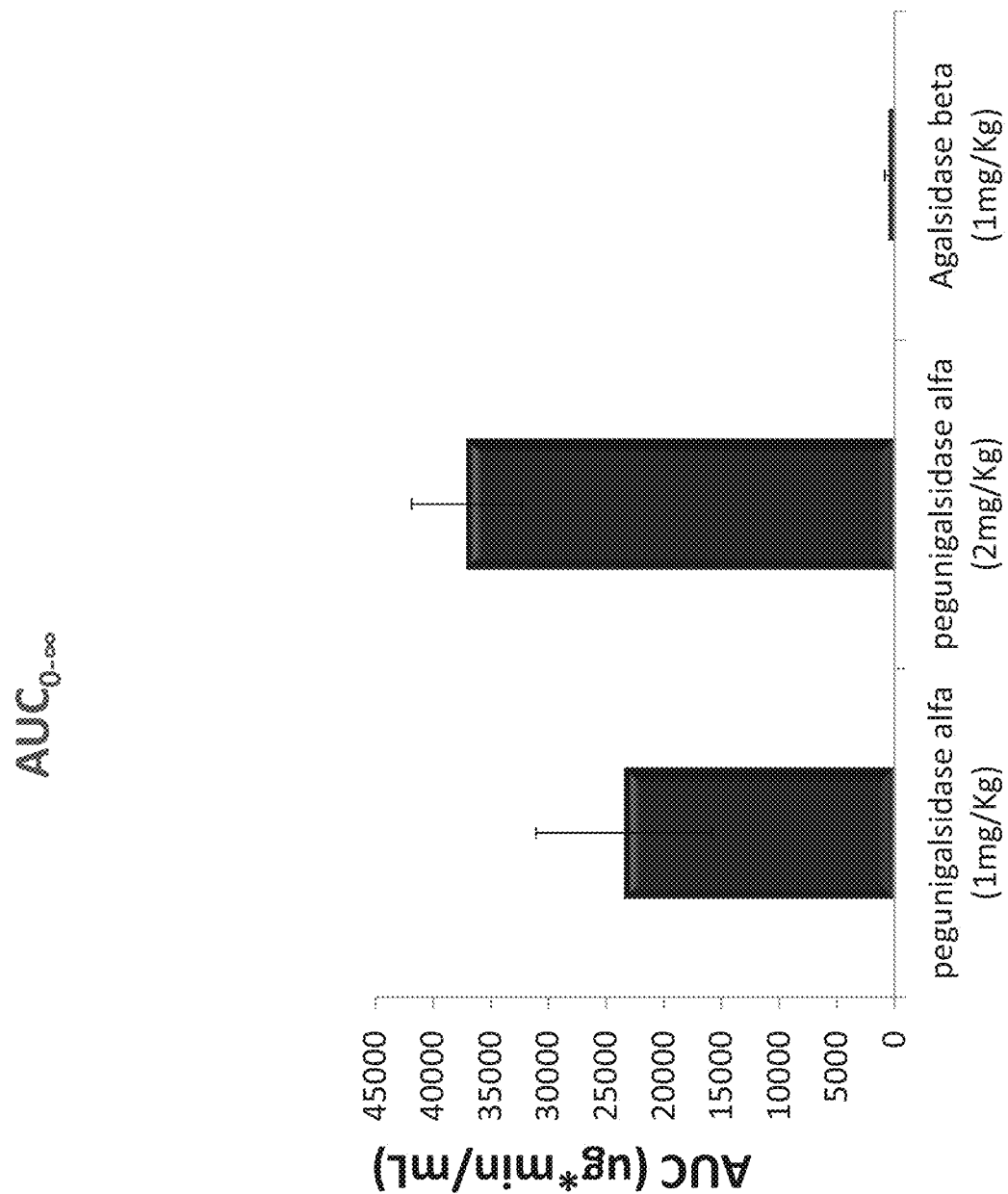

When specific pharmacokinetic variables are assessed, the advantages of pegunigalsidase alfa become even more evident. Both maximal plasma concentration of the enzyme following administration ($C_{max}$, FIG. 3A) and the total bioavailability (area under the plasma versus time curve, extrapolated to infinity, $AUG_{0-\infty}$, expressed as mass (e.g. ug or ng) enzyme x time (e.g. min or hour) per ml plasma, FIG. 3C) are dosage dependent and consistent with the overall pharmacokinetic profile illustrated in FIG. 1. When compared with Agalsidase beta, both the $C_{max}$ and $AUC_{0-\infty}$ of pegunigalsidase alfa are clearly superior to the commercially available enzyme. Half-life ($t_{1/2}$) of pegunigalsidase alfa, at every dosage, was nearly two orders of magnitude greater than that of clinically approved, commercially available Agalsidase beta (Fabrazyme™, Genzyme Corp, Cambridge MA) and Agalsidase alfa (Replagal™, Shire Human Genetic Therapies (HGT), Inc., Cambridge, MA, USA) (FIG. 3B).

Table I below shows the detailed values for the pharmacokinetic parameters of pegunigalsidase alfa:

TABLE I

Pegunigalsidase alfa Pharmacokinetic Parameters

| | Mean ± SE | | | |
|---|---|---|---|---|
| Dose (n) | $AUC_{0-\infty}$ (ng · hr/mL) | $C_{max}$ (ng/mL) | $C_{2\,wk}$ (ng/mL) | $t_{1/2}$ (hr) |
| 0.2 mg/Kg | 70,070 ± 10,632 | 1,858 ± 217 | 21.0 ± 10.5 | 60.3 ± 8.0 |
| 1 mg/Kg | 390,896 ± 55,716 | 11,123 ± 984 | 130 ± 28 | 78.9 ± 4.2 |
| 2 mg/Kg | 619,393 ± 79,281 | 16,625 ± 2,150 | 193 ± 142 | 70.7 ± 9.0 |

Extrapolation of the plasma concentration at 14 days past the 14 day period, considering the half-life of pegunigalsidase alfa (see FIG. 3B) indicates that even at day 21, and day 28 or later, significant potential therapeutic amounts of pegunigalsidase alfa are expected to remain in the patients' plasma.

Example IV

Immunogenicity and Bioavailability of Cross-Linked prh-alpha-GAL-I-CL45

Serum samples were taken once a month for 4 first months and then once every 2 months. 144 samples were analyzed of which 123 were negative for anti-drug antibodies (ADA). Confirmed positive samples were further characterized for neutralizing activity, anti-glycan and anti PEG antibodies.

A low incidence of anti-cross-linked prh-alpha-GAL-I-CL45 antibody formation was reported. Three patients (19%) were identified as treatment-induced ADA positive in at least one visit, with two out of the three having neutralizing antibodies. The ADA presence was transient and no ADA were found in any of these patients following 6-15 month of treatment. Significantly, after 12 month's treatment, none of the patients in the cohort receiving 2.0 mg/Kg cross-linked prh-alpha-GAL-I-CL45 developed treatment-induced anti-cross-linked prh-alpha-GAL-I-CL45 antibodies.

Without wishing to be limited to a single hypothesis, these results suggest that repeated treatments with cross-linked prh-alpha-GAL-I-CL45, which, by virtue of its improved stability provides continuous exposure, can lead to induction of immune tolerance.

Example V

Enhanced Pharmacokinetics of Cross-Linked Pegunigalsidase Alfa and an Extended Dosage Regimen: Multicenter Open Label Switch Over Study Conventional enzyme replacement therapy for Fabry disease patients calls for administration of the drug at maximal intervals of two weeks (14 day) between treatments. Extension of the interval between treatments, without significant reduction in the clinical efficacy of the treatment or increase in treatment-associated adverse events, can be of great clinical importance, reducing the number of interventions and improving patient compliance. In view of the enhanced pharmacokinetics observed in Fabry disease patients receiving bi-weekly infusions of pegunigalsidase alfa, the effect of an extended dosage regimen can be assessed.

Patient selection for the study can be made according to the inclusion and exclusion criteria options including, but not limited to: Treatment of Fabry patients without severe symptoms, relatively slow progressed patient, early diagnosed patients, patients who maintain steady disease symptoms, or keeping a similar deterioration rate for a selected period of time.

Exemplary study inclusion criteria can be, but are not limited to patients with confirmed Fabry disease, as defined by, for example, alpha galactosidase activity and genetic tests, with mild to moderate symptoms as defined in accordance to, for example, the patient's eCFR and eGFR slope, patients aged 16-65 years, at least 3 years on ERT.

Clinical laboratory assessment, monitoring of safety and efficacy variables and adverse events, and recording of pharmacokinetic parameters are performed as detailed in Example I, altered as required for the extended interval between treatments (for example, samples are taken at first and last infusions at time points: pre-infusion (baseline); 1 hour after the beginning of the infusion; at the end of the infusion; 1, 4, 8, 24, 48±3, 72±3, 96±3 hours, 2 weeks ±3 days and 3 weeks ±3 days post-infusion (last blood sample will be drawn just before the second infusion of the patient. Optionally, samples are also taken in the interval between the $2^{nd}$ and $3^{rd}$ week post-infusion, and further optionally, at time points greater than 3 weeks post-infusion, for example, at 4 (four) weeks post infusion ±3 days and/or in the interval between the $3^{rd}$ and $4^{th}$ week post-infusion.

Continued therapeutic plasma levels of pegunigalsidase alfa in patients receiving the tri-weekly or four-weekly dosage, or any dosage at greater than two weeks post-infusion, without significant adverse effects and with maintenance of satisfactory or similar levels of clinical parameters, for example, as in their previous ERT treatment, clinical parameters throughout the duration of the treatment can constitute the basis of a new and improved protocol of extended dosage regimen for enzyme replacement therapy for Fabry disease with pegunigalsidase alfa. Optimal intervals between infusions can be determined (or approximated) from analysis of the clinical data and pharmacokinetic parameters.

Example VI

Projection Analysis for 2 mg/kg Pegunigalsidase Alfa Versus 1 mg/Kg Fabrazyme®

In order to determine the probable pharmacokinetic characteristics of pegunigalsidase alfa when the interval between administrations is extended from 2 weeks to 3 or 4 weeks, and to compare estimated pegunigalsidase alfa exposure to estimated Fabrazyme exposure, a projection analysis was performed.

Kinetics of Cross-Linked prh-alpha-GAL-I-CL45 (Pegunigalsidase Alfa)

The data from patients receiving 2 mg/kg pegunigalsidase alfa (n=4) shown in Example 1 was used for the main part of the projections for pegunigalsidase alfa. Projections generally depend on linear dose-proportionality. As a starting point for these projections, the 3-month data was chosen. The half-life values at 3 months ranged from 70.1 to 105 hours for the four subjects.

Since there were measurable concentrations pre-dose at 3 months due to the previous dose of pegunigalsidase alfa, the pre-dose concentrations were extrapolated to each of the sampling times using the terminal elimination rate ($\lambda z$) value for each subject. These extrapolated concentrations were subtracted from the measured concentrations to arrive at concentrations that were due to the dose administered at 3 months. The adjusted 3-month data for each subject was fit to a 2-compartment model using Phoenix WinNonlin Software. The mean estimates for the model variables were used to simulate three successive doses of 2 mg/kg at intervals of 2, 3 or 4 weeks. The hypothetical infusion time was 6 hours. The values for $C_{max}$, $AUC_{tau}$ (the area for the time between doses), and $C_{min}$ (the concentration before the subsequent dose) are shown in Table II.

TABLE II

Pharmacokinetic Parameters for Projections

| | $1^{st}$ administration (2 mg/Kg) | | | |
|---|---|---|---|---|
| Interval | $C_{max}$ (ng/mL) | $AUC_{tau}$ (ng · hr/mL) | $C_{ave}$* (ng/mL) | $C_{min}$** (ng/mL) |
| q 2 weeks | 22,213 | 1,108,471 | 3,299 | 207 |
| q 3 weeks | 22,213 | 1,123,108 | 2,228 | 25 |
| q 4 weeks | 22,213 | 1,124,907 | 1,457 | 3 |

*Average concentration over dosing interval of 2, 3 or 4 weeks.
**Concentration at the last sampling time before the next administration; either 2, 3, or 4 weeks after the start of the infusion.

PharmacoKinetics of Fabrazyme

Fabrazyme PK parameters were taken from the package insert and in a publication by Eng et al, 2001 (*Am J Hum Genet*, 68:711-722) FIG. 2.

Partial AUC and $C_{ave}$

Table III shows a comparison of projected pharmacokinetic parameters following various dosing regimens of pegunigalsidase alfa and Fabrazyme at 1 mg/kg every 2 weeks.

Data for pegunigalsidase alfa was obtained from the on-going phase I/II study. Information on the pharmacokinetic characteristics of Fabrazyme is available in the package insert and in a publication by Eng et al, 2001 (*Am J Hum Genet*, 68:711-722). Projection modeling was done using Phoenix WinNonlin Software (Ver. 6.3)

The weekly Partial AUC and $C_{ave}$ calculations enabled the comparison evaluation/estimation of the drug availability on weeks 1, 2, 3 and 4 of pegunigalsidase alfa and comparison to Fabrazyme every two weeks The data is calculated per week and presented sequentially. Thick lines represent the time of the repeated administration. Thus, for the 2 week interval the $3^{rd}$, $5^{th}$ and $7^{th}$ line represent dose administration, for the $3^{rd}$ week interval the $4^{th}$ $7^{th}$ and $10^{th}$ line represent dose administration, etc). The gray and white boxes visually define the different infusion intervals. The mean weekly enzyme concentrations, at 168 hours (1 week) and 336 hours (2 weeks), were interpolated or extrapolated in order to estimate drug coverage by week. As shown in the table: For pegunigalsidase alfa, 2 mg/kg, every 2, 3, or 4 weeks, the weekly $C_{ave}$ values (709, 87 and 11 ng/ml, respectively) are significantly higher than the negligible $2^{nd}$ week $C_{ave}$ values for Fabrazyme.

Fabrazyme $C_{ave}$ levels following 10 hrs after the infusion are similar to pegunigalsidase alfa estimated $C_{ave}$ levels at the 4th week following administration of 2 mg/kg, every 4 weeks (11 ng/mL).

Figure 4A:
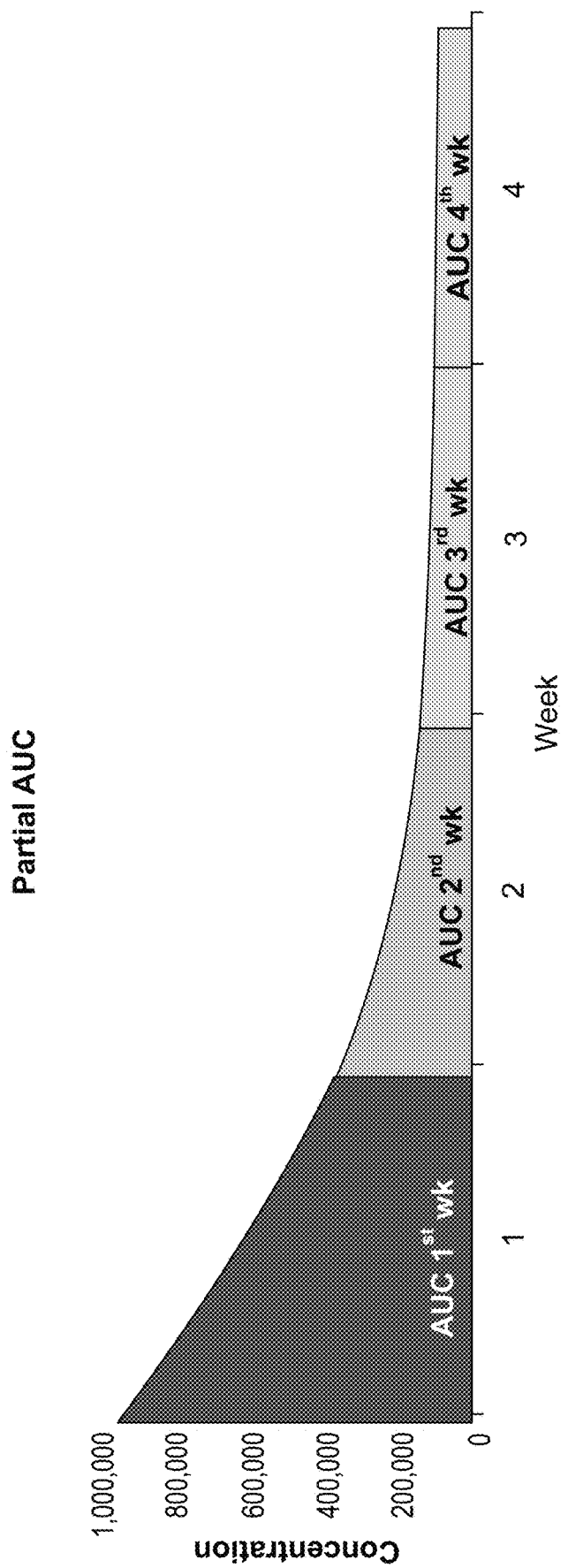
FIGS. 4A-4B are graphic representations of enzyme availability modeling over a 4 week period derived from a single infusion of pegunigalsidase alfa, comparing availability modeling with an extended regimen (2 mg/Kg once every 4 weeks) of pegunigalsidase alfa with modeling of the standard regimen of agalsidase beta (Fabrazyme)(1 mg/Kg once every 2 weeks).
Figure 4B:
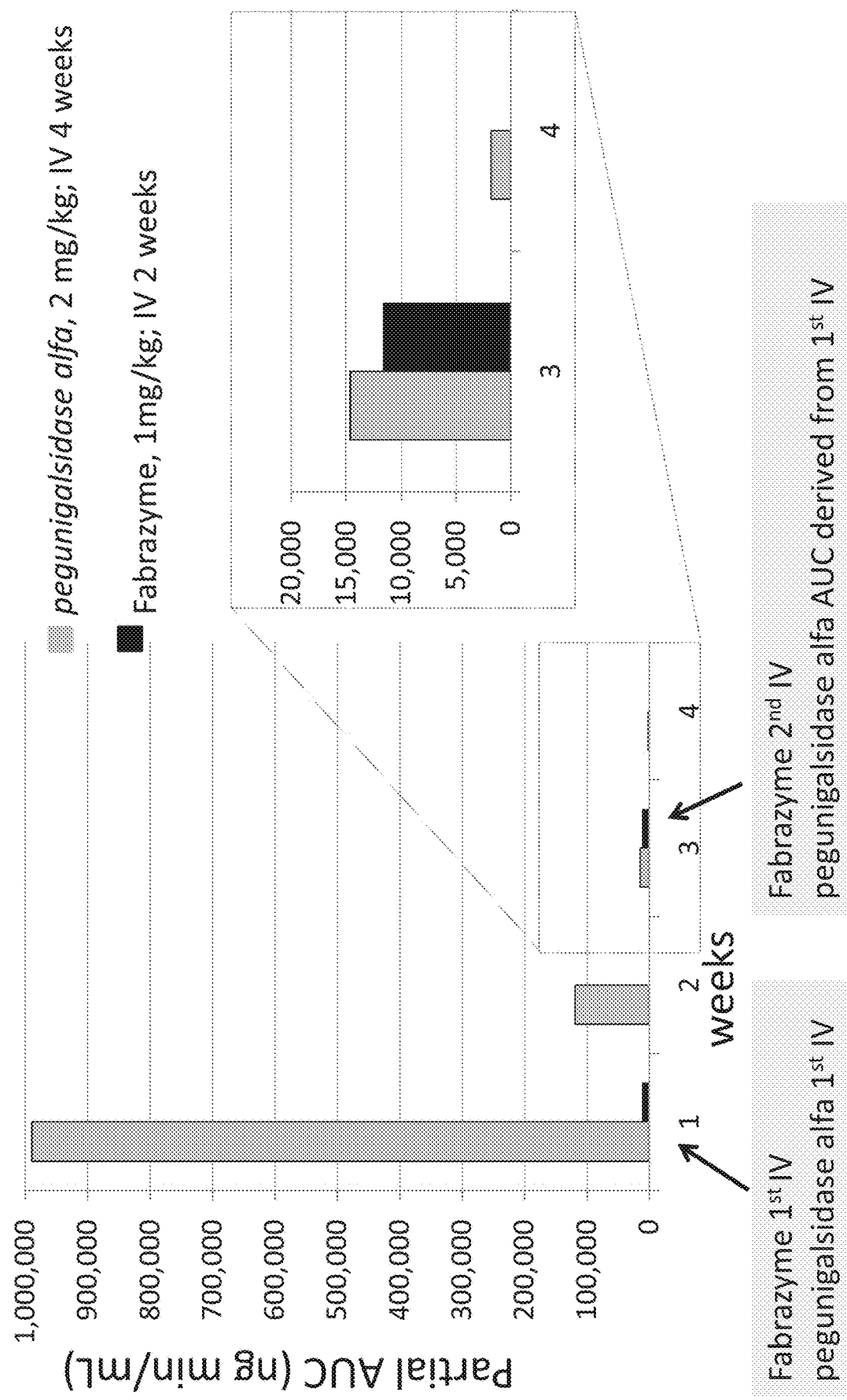

FIG. 4A graphically illustrates extrapolated enzyme availability (plasma concentration) over a four week period following a single infusion of 2 mg/Kg pegunigalsidase alfa. When the projected AUC following treatment with pegunigalsidase alfa over a four week period is compared with that of Fabrazyme administered bi-weekly, over the same period, maintenance of enzyme availability for pegunigalsidase alfa is clearly superior to that of Fabrazyme (see FIG. 4B, particularly inset).

The results show that in contrast to Fabrazyme, significant levels of enzyme are expected to remain in the circulation for the entire duration of treatment, available to reach the target organs, following administration of 2 mg/Kg of pegunigalsidase alfa at 3 and 4 week infusion intervals.

TABLE III

Partial Areas and $C_{ave}$ by Week for 12 Weeks of Treatment

| | Fabrazyme, 1 mg/kg, q 2 weeks | | Pegunigalsidase alfa, 2 mg/kg, | | | | | |
|---|---|---|---|---|---|---|---|---|
| | | | q 2 weeks | | q 3 weeks | | q 4 weeks | |
| Time (week) | Partial AUC (week) (ng · hr/mL) | $C_{ave}$ for week (ng/mL) | Partial AUC (week) (ng · hr/mL) | $C_{ave}$ for week (ng/mL) | Partial AUC (week) (ng · hr/mL) | $C_{ave}$ for week (ng/mL) | Partial AUC (week) (ng · hr/mL) | $C_{ave}$ for week (ng/mL) |
| 1 | 11,667 | 69 | 989,406 | 5,889 | 989,406 | 5,889 | 989,406 | 5,889 |
| 2 | nil | nil | 119,065 | 709 | 119,065 | 709 | 119,065 | 709 |
| 3 | 11,667 | 69 | 1,004,012 | 5,976 | 14,637 | 87 | 14,637 | 87 |
| 4 | nil | nil | 120,864 | 719 | 991,201 | 5,900 | 1,799 | 11 |
| 5 | 11,667 | 69 | 1,004,233 | 5,978 | 119,286 | 710 | 989,627 | 5,891 |
| 6 | nil | nil | 120,892 | 720 | 14,664 | 87 | 119,092 | 709 |
| 7 | 11,667 | 69 | 1,004,233 | 5,978 | 991,205 | 5,900 | 14,640 | 87 |
| 8 | nil | nil | 120,892 | 720 | 119,287 | 710 | 1,800 | 11 |
| 9 | 11,667 | 69 | 1,004,233 | 5,978 | 14,664 | 87 | 989,627 | 5,891 |
| 10 | nil | nil | 120,892 | 720 | 991,205 | 5,900 | 119,092 | 709 |
| 11 | 11,667 | 69 | 1,004,233 | 5,978 | 119,287 | 710 | 14,640 | 87 |
| 12 | nil | nil | 120,892 | 720 | 14,664 | 87 | 1,800 | 11 |

Taken together, the results provided herein indicate that the pharmacokinetic properties of the cross-linked alpha-galactosidase pegunigalsidase alfa are different and advantageous compared to those of both mammalian cell-derived currently approved, commercially available Fabry ERTs Agalsidase beta (Fabrazyme™, Genzyme Corp, Cambridge MA) and Agalsidase alfa (Replagal™, Shire Human Genetic Therapies (HGT), Inc., Cambridge, MA, USA). The longer half-life ($t_{1/2}$) and substantially greater overall bioavailability ($AUC_{0-\infty}$) observed for all dosages of pegunigalsidase alfa reflect the presence of available active enzyme throughout the 2 weeks between infusions (administrations). The improved pharmacokinetic profile indicate that it is suitable for effective long term enzyme replacement therapy for Fabry disease and can be administered at intervals of at least 2 weeks to every 4 weeks.

Example VII

Clinical Trial Protocol: A Phase 3, Oven Label, Switch Over Study to Evaluate the Safety, Efficacy and Pharmacokinetics of Pegunigalsidase Alfa, Administered by Intravenous Infusion Every 4 Weeks to Adult Fabry Patients Currently Treated with ERT: Fabrazyme® (Agalsidase Beta) or Replagal® (Agalsidase Alfa)

This study assesses the safety, efficacy and pharmacokinetics of plant recombinant human α-galactosidase cross-linked with bis-NHS-PEG$_{45}$ (prh-alpha-GAL-I-CL45) (pegunigalsidase alfa) in patients with Fabry disease currently treated with commercially available ERT (agalsidase alfa or agalsidase beta). Subjects are required to have a definitive diagnosis of Fabry disease based on alpha-GAL-A activity (males) or genetic testing (females) with manifestations of the disease, and to have been treated with ERT for at least 3 years. The plant recombinant human α-galactosidase cross-linked with bis-NHS-PEG$_{45}$ (prh-alpha-GAL-I-CL45) (pegunigalsidase alfa) will be administered in a dose of 2 mg/kg every four (4) weeks, for 52 weeks. The parameters chosen as endpoints are the parameters most relevant to the disease and allow a significant and relevant evaluation of the safety, pharmacokinetics and efficacy endpoints.

Drug Dosage and Administration:

Upon confirmation of eligibility, patients are to be switched to pegunigalsidase alfa 2 mg/kg, administered intravenously, every 4 weeks. Infusion time with pegunigalsidase alfa varies according to the weight of the patient pending: patient tolerability, Investigator evaluation, and Sponsor Medical Monitor/Director's approval and after an attempt to taper down gradually used pre-medication.

Pharmacokinetics (PK) Parameters

The following PK parameters are derived from the plasma concentration versus time profiles to determine the PK profile of the study drug: $C_{max}$, $t_{1/2}$, $T_{max}$, $AUC_{0-t}$, and $AUC_{0-\infty}$. Blood for PK analysis will be drawn on Day 1 and at the conclusion of treatment (52 weeks). On the days of blood draws, blood samples are taken at the following time points: pre-infusion (baseline); 1 hour after the beginning of the infusion; at the end of the infusion; 1±0.25, 2±0.25, 4±0.25, 8±0.25, 24±0.5, 48±3 and 96±3 hours post-infusion and at 14±3, 21±3 and 28±3 days post-infusion (last blood sample will be drawn just before the next infusion of the patient)(a total of 13 time points within 28 days).

Efficacy Variable(s)

Efficacy parameters evaluated for analysis of endpoints are as follows:
1. Estimated glomerular filtration rate (eGFR$_{CKD-EPI}$)
2. Left Ventricular Mass Index (g/m$^2$) by echocardiogram
3. Globotriaosylsphingosine (Lyso-Gb3) concentration in plasma
4. Gb3 concentrations in plasma
5. Urine Lyso-Gb3
6. Protein/Creatinine ratio spot urine test
7. Frequency of pain medication used
8. Exercise tolerance (stress test)
9. Short Form Brief Pain Inventory (BPI)
10. Mainz Severity Score Index (MSSI)
11. Quality of Life EQ-5D-5L Safety Variables Safety is assessed by changes from baseline in: clinical laboratory tests, physical examination, assessment of injection site after drug administration, electrocardiogram (ECG), frequency, severity, and duration of treatment-emergent AEs (adverse events), ability to taper off infusion pre-medication, requirement for use of pre-medication overall to manage infusion reactions and treatment-induced anti-pegunigalsidase alfa antibodies.

Previous results have revealed a longer half-life ($t_{1/2}$) and substantially greater overall bioavailability ($AUC_{0-\infty}$) for pegunigalsidase alfa in all doses at a bi-weekly infusion (administration) regimen. Extended dosage intervals can have significant impact on the convenience, cost, compliance rate and frequency of adverse effects of ERT for Fabry disease. In order to evaluate the suitability of plant recombinant human α-galactosidase cross-linked with bis-NHS-PEG$_{45}$ (prh-alpha-GAL-I-CL45) (pegunigalsidase alfa) for effective long term enzyme replacement therapy for Fabry disease, pegunigalsidase alfa is administered at intervals of every 4 weeks.

In the open-label switchover study assessing safety, efficacy, and pharmacokinetics of pegunigalsidase alfa treatment of 2 mg/kg every 4 weeks in patients previously treated with ERT, agalsidase alfa or agalsidase beta, for at least 3 years and on a stable dose (>80% labeled dose/kg) for at least the last 6 months will be enrolled and switched from their current ERT to receive intravenous (IV) infusions of pegunigalsidase 2 mg/kg every 4 weeks for 52 weeks (total of 14 infusions).

Significant evidence of maintenance of the enhanced pharmacokinetic properties of the cross-linked alpha-galactosidase pegunigalsidase alfa over the 4 week interval from infusion to infusion will aid in establishing that the cross-linked alpha-galactosidase pegunigalsidase alfa is different and advantageous compared to other currently approved, commercially available Fabry ERTs Agalsidase beta (Fabrazyme™, Genzyme Corp, Cambridge MA) and Agalsidase alfa (Replagal™, Shire Human Genetic Therapies (HGT), Inc., Cambridge, MA, USA).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating Fabry disease in a human subject in need thereof, the method comprising administering to the subject a therapeutically effective amount of recombinant human α-galactosidase A, wherein said therapeutically effective amount of said recombinant human α-galactosidase A is 2.0 mg/Kg body weight, thereby treating Fabry disease in the subject, wherein said administering is effected in intervals of 4 weeks and wherein said recombinant human a-galactosidase A is plant recombinant human α-galactosidase A cross-linked with bis-NHS-PEG$_{45}$, and wherein said subject is a subject maintaining a similar rate of deterioration in at least one Fabry disease parameter following administration of said recombinant human α-galactosidase A at the indicated dosage of 2.0 mg/kg body weight at intervals of 4 weeks.

2. The method of claim 1, wherein administration of said therapeutically effective amount of recombinant human α-galactosidase results in at least one of the following in said subject:
(i) attenuation of deterioration of cardiac parameters Left Ventricle Mass (LVM) or Left Ventricle Mass Index (LVMI);
(ii) attenuation of Fabry disease-related deterioration of kidney function;
(iii) attenuation of deterioration of at least one gastrointestinal parameter; or (iv) attenuation of deterioration of a Mainz Severity Score Index (MSSI) score.

3. The method of claim 1, wherein said recombinant human α-galactosidase A has a circulating half-life ($T_{1/2}$) of at least 50 hours following administration.

4. The method of claim 1, wherein said recombinant human α-galactosidase A has a $C_{max}$ of at least 8000 ng/ml following administration of 2 mg/Kg body weight.

5. The method of claim 1, wherein said recombinant human α-galactosidase A has a bioavailability ($AUC_{0-\infty}$) of at least 400,000 ng*hr/ml following administration of 2.0 mg/Kg body weight of said recombinant human α-galactosidase A.

6. The method of claim 1, wherein administration of said therapeutically effective amount of recombinant human α-galactosidase A in intervals of 4 weeks does not result in de novo serum anti-recombinant human α-galactosidase A antibodies after 12 months of treatment.

* * * * *